US008314212B2

(12) United States Patent
Miles et al.

(10) Patent No.: US 8,314,212 B2
(45) Date of Patent: Nov. 20, 2012

(54) PLASMINOGEN RECEPTOR PLG-RKT AND ANTIBODIES THEREOF

(75) Inventors: Lindsey A. Miles, San Diego, CA (US); John Yates, San Diego, CA (US); Emily I. Chen, Port Jefferson, NY (US); Nagyung Baik, San Diego, CA (US); Robert J. Parmer, San Diego, CA (US)

(73) Assignee: Lindsey Miles, La Jolla, CA (US)

( * ) Notice: Subject to any disclaimer, the term of this patent is extended or adjusted under 35 U.S.C. 154(b) by 0 days.

(21) Appl. No.: 12/866,520

(22) PCT Filed: Feb. 6, 2009

(86) PCT No.: PCT/US2009/000744
§ 371 (c)(1),
(2), (4) Date: Aug. 6, 2010

(87) PCT Pub. No.: WO2009/099631
PCT Pub. Date: Aug. 13, 2009

(65) Prior Publication Data
US 2010/0316648 A1 Dec. 16, 2010

Related U.S. Application Data

(60) Provisional application No. 61/065,109, filed on Feb. 8, 2008.

(51) Int. Cl.
*C07K 16/00* (2006.01)
(52) U.S. Cl. .............. 530/387.9; 530/387.1; 530/388.22
(58) Field of Classification Search .................. None
See application file for complete search history.

(56) References Cited

U.S. PATENT DOCUMENTS

| | | | |
|---|---|---|---|
| 5,501,853 A | 3/1996 | Haigwood et al. | |
| 7,585,937 B2 * | 9/2009 | Kungl ............................ | 530/324 |
| 7,595,047 B2 * | 9/2009 | Moser et al. ................ | 424/141.1 |
| 8,003,096 B2 * | 8/2011 | Carmeliet et al. .......... | 424/94.63 |
| 2006/0147441 A1 | 7/2006 | Morikawa et al. | |
| 2010/0047256 A1 * | 2/2010 | Lundberg et al. .......... | 424/172.1 |

OTHER PUBLICATIONS

"International Application Serial No. PCT/US2009/000744, International Preliminary Report mailed Aug. 19, 2010", 8 pgs.
Bern, M., et al., "Automatic Quality Assessment of Peptide Tandem Mass Spectra", Bioinformatics, 20(suppl 1), (2004), i49-i54.
Bordier, C., "Phase separation of integral membrane proteins in Triton X-114 solution", J Biol Chem., 256(4), (Feb. 25, 1981), 1604-7.
Correc, P., et al., "The presence of plasmin receptors on three mammary carcinoma MCF-7 sublines", Int J Cancer, 46(4), (Oct. 15, 1990), 745-50.
Creemers, E., et al., "Disruption of the plasminogen gene in mice abolishes wound healing after myocardial infarction", Am J Pathol., 156(6), (Jun. 2000), 1865-73.
Eng, J. K., et al., "An approach to correlate tandem mass spectral data of peptides with amino acid sequences in a protein database", Journal of the American Society for Mass Spectrometry, 5, (1994), 976-989.
Estreicher, A., et al., "Characterization of the cellular binding site for the urokinase-type plasminogen activator", J Biol Chem., 264(2), (Jan. 15, 1989), 1180-9.
Felez, J., et al., "Characterization of cellular binding sites and interactive regions within reactants required for enhancement of plasminogen activation by tPA on the surface of leukocytic cells", Thromb Haemost., 76(4), (Oct. 1996), 577-84.
Felez, J., et al., "Competition between plasminogen and tissue plasminogen activator for cellular binding sites.", Blood, 82(8), (Oct. 15, 1993), 2433-41.
Harada, J. N, et al., "Identification of novel mammalian growth regulatory factors by genome-scale quantitative image analysis", Genome Res., 15(8), (Aug. 2005), 1136-44.
Hawley, S. B, et al., "Discriminating between cell surface and intracellular plasminogen-binding proteins: heterogeneity in profibrinolytic plasminogen-binding proteins on monocytoid cells", Thromb Haemost., 84(5), (Nov. 2000), 882-90.
Hawley, S. B, et al., "Purification, cloning, and characterization of a profibrinolytic plasminogen-binding protein, TIP49a", J Biol Chem., 276(1), (Jan. 5, 2001), 179-86.
Jacovina, A. T, et al., "Neuritogenesis and the nerve growth factor-induced differentiation of PC-12 cells requires annexin II-mediated plasmin generation", J Biol Chem., 276(52), (Dec. 28, 2001), 49350-8.
Krajewski, S., et al., "Release of caspase-9 from mitochondria during neuronal apoptosis and cerebral ischemia", Proc Natl Acad Sci U S A., 96(10), (May 11, 1999), 5752-7.
Larmann, J. P, et al., "Two-dimensional separations of peptides and proteins by comprehensive liquid chromatography-capillary electrophoresis.", Electrophoresis, 14(5-6), (May-Jun. 1993), 439-47.
Link, A. J, et al., "Direct analysis of protein complexes using mass spectrometry", Nat Biotechnol., 17(7), (Jul. 1999), 676-82.

(Continued)

*Primary Examiner* — Shulamith H Shafer
(74) *Attorney, Agent, or Firm* — Schwegman Lundberg Woessner P.A.

(57) ABSTRACT

The invention relates to C9orf46 homolog, a novel murine membrane protein, and its orthologs in human, mouse and all other species, termed Plg-$R_{KT}$, or analogs, thereof and the isolation method. The function of this molecule is to bind to plasminogen, plasminogen fragments such as angiostatin[1] and other plasminongen fragments having angiostatic activity, tissue plasminogen activator and Lipoprotein(a). Plasminogen receptors function to modulate cell surface proteolysis and physiological and pathophysiological processes requiring cell migration, including, but not limited to, cell migration during inflammation, tissue remodeling, wound healing, tumor cell invasion and metastasis, skeletal myogenesis, neurite outgrowth. Plasminogen receptors also modulate apoptosis and cell death. The invention also relates to antibodies that inhibit plasminogen, plasminogen fragments such as angiostatin[1] and other plasminongen fragments having angiostatic activity, tissue plasminogen activator or Lipoprotein(a) binding to Plg-$R_{KT}$ and/or immunoreact with Plg-$R_{KT}$.

2 Claims, No Drawings

OTHER PUBLICATIONS

Lopez-Alemany, R., et al., "Plasmin generation dependent on alpha-enolase-type plasminogen receptor is required for myogenesis", Thromb Haemost., 90(4), (Oct. 2003), 724-33.

Lund, L. R, et al., "Lactational competence and involution of the mouse mammary gland require plasminogen", Development, 127(20), (Oct. 2000), 4481-92.

Miles, L. A, et al., "A potential basis for the thrombotic risks associated with lipoprotein(a).", Nature, 339(6222), (May 25, 1989), 301-3.

Miles, L. A, et al., "Plasminogen receptors: the sine qua non of cell surface plasminogen activation", Front Biosci., 10, (May 1, 2005), 1754-62.

Miles, L. A, et al., "Receptor mediated binding of the fibrinolytic components, plasminogen and urokinase, to peripheral blood cells", Thromb Haemost., 58(3), (Oct. 28, 1987), 936-42.

Miles, L. A, et al., "Role of cell-surface lysines in plasminogen binding to cells: identification of alpha-enolase as a candidate plasminogen receptor", Biochemistry, 30(6), (Feb. 12, 1991), 1682-91.

Miles, L. A, et al., "The cell-binding domains of plasminogen and their function in plasma", J Biol Chem., 263(24), (Aug. 25, 1988), 11928-34.

Mitchell, J. W, et al., "Plasminogen inhibits TNFalpha-induced apoptosis in monocytes", Blood, 107(11), (Jun. 1, 2006), 4383-90.

Nguyen, S. T, et al., "Identification of a predictive gene expression signature of cervical lymph node metastasis in oral squamous cell carcinoma.", Cancer Sci., 98(5), (May 2007), 740-6.

Opiteck, G. J, et al., "Two-Dimensional SEC/RPLC Coupled to Mass Spectrometry for the Analysis of Peptides", Anal. Chem., 69(13), (1997), 2283-2291.

Peng, J., et al., "Evaluation of Multidimensional Chromatography Coupled with Tandem Mass Spectrometry (LC/LC-MS/MS) for Large-Scale Protein Analysis:? The Yeast Proteome", Journal of Proteome Research, 2(1), (2003), 43-50.

Ploplis, V. A, et al., "Plasminogen deficiency differentially affects recruitment of inflammatory cell populations in mice", Blood, 91(6), (Mar. 15, 1998), 2005-9.

Pozzi, A., et al., "Elevated matrix metalloprotease and angiostatin levels in integrin alpha 1 knockout mice cause reduced tumor vascularization.", Proc Natl Acad Sci U S A., 97(5), (Feb. 29, 2000), 2202-7.

Ranson, M., et al., "Increased plasminogen binding is associated with metastatic breast cancer cells: differential expression of plasminogen binding proteins.", Br J Cancer, 77(10), (May 1998), 1586-97.

Romer, John, et al., "Impaired Wound Healing in Mice with a Disrupted Plasminogen Gene", Nature Medicine, vol. 2, No. 3, (Mar. 1996), 287-292.

Romer, John, et al., "Plasminogen and wound healing", Nature Medicine, 2, (1996), 725.

Saksela, O., "Plasminogen activation and regulation of pericellular proteolysis", Biochim Biophys Acta., 823(1), (Nov. 12, 1985), 35-65.

Sottrup-Jensen, L., et al., "The primary structure of human plasminogen: isolation of two lysine-binding fragments and one 'mini-' plasminogen (MW 38,000) by elastase-catalyzed-specific limited proteolysis", In: Davidson J F, Rowan R M, Samama M M, Desnoyers P C, eds. Progress in Chemical Fibrinolysis and Thrombolysis, vol. 3., New York: Raven Press, (1978), 191-209.

Su, A. I, et al., "A gene atlas of the mouse and human protein-encoding transcriptomes", Proc Natl Acad Sci U S A., 101(16), (Apr. 20, 2004), 6062-7.

Su, A. I, et al., "Large-scale analysis of the human and mouse transcriptomes", Proc Natl Acad Sci U S A., 99(7), (Apr. 2, 2002), 4465-70.

Swaisgood, C. M, et al., "In vivo regulation of plasminogen function by plasma carboxypeptidase B", J Clin Invest., 110(9), (Nov. 2002), 1275-82.

Tabb, D. L, et al., "DTASelect and Contrast: tools for assembling and comparing protein identifications from shotgun proteomics", J Proteome Res., 1(1), (Jan.-Feb. 2002), 21-6.

Testa, J. E, et al., "Protease receptors on cell surfaces: new mechanistic formulas applied to an old problem.", J Natl Cancer Inst., 80(10), (Jul. 20, 1988), 712-3.

Wang, G. G, et al., "Quantitative production of macrophages or neutrophils ex vivo using conditional Hoxb8", Nat Methods, 3(4), (Apr. 2006), 287-93.

Wolters, D. A, et al., "An Automated Multidimensional Protein Identification Technology for Shotgun Proteomics", Anal. Chem., 73(23), (2001), 5683-5690.

Yates, J. R, "Database searching using mass spectrometry data", Electrophoresis, 19(6), (May 1998), 893-900.

"International Application U.S. Appl. No. PCT/US2009/000744, Search Report mailed Jun. 18, 2009", 7 pgs.

"International Application U.S. Appl. No. PCT/US2009/000744, Written Opinion mailed Jun. 18, 2009", 7 pgs.

"NCBI Database Entry Q9D3P8", Retrieved from:hllp:llwww.ncbi.nlm.nih.gov/protein/68565281, (Jul. 5, 2005).

Lahteenmaki, et al., "Bacterial plasminogen activators and receptors.", FEMS Microbiology Rev iews, vol. 25, 531-552, 2001.

Parmer, et al., "Receptor recognition specificity of plasminogen for the novel plasminogen receptor", Pig-RKT. The FASEB Journa l. Apr. 2008:22 :903.5.

Plow, et al., "The cell biology of the plasminogen system", FASEB J,vol. 9, (1995), 939-945.

* cited by examiner

PLASMINOGEN RECEPTOR PLG-RKT AND ANTIBODIES THEREOF

PRIORITY

This application is a U.S. National Stage Filing under 35 U.S.C. 371 from International Patent Application Serial No. PCT/US2009/000744, filed Feb. 6, 2009, and published on Aug. 13, 2009 as WO 2009/099631, which claims priority to U.S. provisional application Ser. No. 61/065,109, filed Feb. 8, 2008, the contents of which are incorporated herein by reference in their entirety.

GOVERNMENT FUNDING

This invention was made with government support under Grant Nos. HL38272, HL45934 and HL081046, awarded by the National Heart, Lung, and Blood Institute, National Institutes of Health.

TECHNICAL FIELD

The present invention relates to C9orf46 homolog, a novel murine membrane protein, and its orthologs in human and all other species including mouse, termed Plg-$R_{KT}$, or polypeptide analogs, thereof. The present invention also relates to polyclonal and monoclonal antibodies that detect C9orf46 homolog/Plg-$R_{KT}$ and/or inhibit its functions. The present invention also relates to a method for identification of cell surface receptors.

BACKGROUND

Localization of plasminogen and plasminogen activators on cell surfaces arms cells with the proteolytic activity of plasmin. Cell surface proteolysis by plasmin is an essential feature of physiological and pathological processes requiring extracellular matrix degradation for cell migration [2,3], notably macrophage recruitment during the inflammatory response [4], as well as tissue remodeling [5], wound healing [6,7], tumor cell invasion and metastasis [8] and skeletal myogenesis [9], neurite outgrowth [10] and apoptosis [11]. Furthermore, localization of plasminogen on the cell surface is required to facilitate macrophage recruitment in vivo [12]. However, the specific molecules that account for the increased plasminogen binding capacity of the cells following differentiation to macrophages have not been elucidated.

Proteins exposing carboxyl-terminal lysines on cell surfaces are responsible for the ability of eukaryotic cells to bind plasminogen and enhance plasminogen activation because carboxypeptidase B (CpB) only partially reduces the plasminogen binding capacity of cells but completely blocks the cell-dependent stimulation of plasminogen activation [13]. Thus, a specific subset of plasminogen binding sites, with carboxyl terminal lysines, is entirely responsible for the ability of cells to promote plasminogen activation. [These binding sites also interact with tissue plasminogen activator [14], lipoprotein(a) [15] and plasminogen fragments such as angiostatin [1].] Also in vivo results show that CpB-sensitive plasminogen receptors mediate monocyte recruitment in response to inflammatory stimuli [12]. Therefore, the ideal candidate for a plasmin(ogen) receptor is an integral membrane protein that exposes a carboxyl terminal lysine on the cell surface. Such a protein has not been identified, to our knowledge.

A number of cell surface proteins with carboxyl terminal lysines have been identified as plasminogen binding proteins on cell surfaces of a variety of cell types [16]. However, most proteins that have been identified do not have signal sequences and are known to be expressed intracellularly. No integral membrane protein with a carboxyl terminal lysine has been identified as a plasminogen receptor. A major difficulty in the field is that isolation and characterizations have been performed using SDS gels that are not ideal for resolution of integral membrane proteins.

Therefore, in order to search for an integral membrane protein with a carboxyl terminal lysine we employed a novel purification procedure followed by multidimensional protein identification technology (MudPIT). Intact cells were biotinylated and then either untreated or treated with CpB (to remove carboxyl terminal lysines). Then membrane fractions were prepared and isolated by affinity chromatography on plasminogen-Sepharose. The proteins that bound specifically to plasminogen-Sepharose were then captured on avidin-Sepharose, digested with trypsin and subjected to multidimensional protein identification technology (MudPIT). (Proteins that were not detected following treatment of intact cells with CpB were plasminogen binding proteins exposing C-terminal basic residues on the cell surface.) We identified a novel protein, C9orf46 homolog, that is predicted to be a Type II transmembrane protein that exposes a carboxyl terminal lysine on the cell surface, the first such candidate plasminogen receptor with this structure. We named the protein Plg-$R_{KT}$, to refer to murine, human and all other orthologs. Furthermore, Plg-$R_{KT}$ expression was markedly upregulated when progenitor monocytes were differentiated with macrophage colony stimulating factor.

Our identification of peptides corresponding to Plg-$R_{KT}$ is, to our knowledge, the first demonstration of the existence of a protein encoded by the C9orf46 homolog gene present in the murine genome. The C9orf46 homolog DNA sequence encodes a protein of 147 amino acids with a calculated molecular weight of 17,261 Da. Notably, a carboxyl terminal lysine is present, consistent with the CpB sensitivity of this protein (on intact cells) in our isolation method and consistent with Plg-$R_{KT}$ as a candidate profibrinolytic plasminogen receptor. The Plg-$R_{KT}$ sequence is predicted to be a Type II (multipass) transmembrane protein with two predicted transmembrane domains from $F_{53}$-$L_{73}$ and $P_{78}$—$Y_{99}$. Hence, a 27 amino acid carboxyl terminal tail with a carboxyl terminal lysine is predicted to be exposed on the cell surface, again, consistent with our identification method, and placing the carboxyl terminal lysine in an orientation to bind plasminogen on the cell surface. We blasted the C9orf46 homolog/Plg-$R_{KT}$ sequence against all species using NCBI Blast and obtained unique human, rat, dog and cow orthologs, with high homology (e.g. human versus mouse=96% homology), high identity and no gaps in the sequence. Of key importance, a C-terminal lysine is predicted for all of the mammalian orthologs obtained in the blast search. In a query of the Ensembl Gene Report, DNA sequences of all other available mammalian orthologs (armadillo, lesser Madagascar hedgehog, rhesus monkey, gray short tailed opossom, domestic rabbit and chimpanzee) encoded C-terminal lysines, supporting functional importance of this residue.

The C9orf46 homolog/Plg-$R_{KT}$ transcript is broadly expressed in normal human and mouse tissues, [as determined using high-throughput gene expression profiling in which RNA samples from human and murine tissues were hybridized to high-density gene expression arrays [17,18]] including spleen, thymus, lymph node, lung, intestine, bone marrow, as well as endocrine tissue, adrenal, pituitary vascular tissue, kidney, liver, stomach, bladder, and neuronal tissue (hippocampus, hypothalamus, cerebellum, cerebral cortex, olfactory bulb and dorsal root ganglion).

We searched for C9orf46 homolog/Plg-$R_{KT}$ mRNA microarray expression data in the European Bioinformatics Institute ArrayExpress Archive database. C9orf46 homolog mRNA is present in monocytes, leukocytes, NK cells, T cells, myeloid, dendritic, and plasmacytoid cells, breast cancer, acute lymphoblastic leukemia and Molt-4 acute lymphoblastic leukemia cells. These data are consistent with previous reports documenting expression of plasminogen binding sites on peripheral blood leukocytes[19], breast cancer cells[8,20] and other tissues [reviewed in [16]]. In addition, results obtained by searching the ArrayExpress Warehouse indicated that the C9orf46 homolog gene is also regulated in other tissues by lipopolysaccharide, aldosterone, canrenoate, $H_2O_2$, and dexamethasone. The broad distribution and regulation in tissues that express plasminogen binding sites, suggest that Plg-$R_{KT}$ provides plasminogen receptor function that may serve to modulate plasmin proteolytic functions in these tissues, as well. In genome-scale quantitative image analysis, overexpression of more than 86 cDNAs, including C9orf46 homolog, conferred dramatic increases in cell proliferation, while knockdown of C9orf46 homolog mRNA resulted in apoptosis[21]. In microarray studies, C9orf46 homolog mRNA expression has a high power to predict cervical lymph node metastasis in oral squamous cell carcinoma.

It is likely that Plg-$R_{KT}$ has not been identified previously because, being a membrane protein, it did not resolve well in SDS gel electrophoresis, the technique that has been used predominantly in the plasminogen receptor field for protein discovery. Furthermore, Plg-$R_{KT}$ represents the first plasminogen-binding protein that is a Type II membrane protein with a carboxyl terminal lysine on the extracellular face of the membrane in an orientation available to interact with plasminogen and in a location that can serve to localize plasminogen and plasmin to the cell surface.

BRIEF SUMMARY OF THE INVENTION

A novel murine membrane protein, C9orf46 homolog and its orthologs in human, mouse and all other species, termed Plg-$R_{KT}$, has been discovered. The function of this molecule is to bind to plasminogen, plasminogen fragments, tissue plasminogen activator and lipoprotein(a). Plasminogen receptors function to modulate cell surface proteolysis and physiological and pathophysiological processes requiring cell migration, including, but not limited to, cell migration during inflammation, tissue remodeling, wound healing, tumor cell invasion and metastasis, skeletal myogenesis, neurite outgrowth. Plasminogen receptors also modulate apoptosis and cell death.

Thus, the present invention contemplates a variety of Plg-$R_{KT}$ polypeptides comprising no more than 50 amino acid residues that have the capacity to inhibit the binding of plasminogen, plasminogen fragments, tissue plasminogen activator and/or lipoprotein(a) to Plg-$R_{KT}$.

In a related embodiment, the present invention contemplates an antibody comprising antibody molecules that inhibit the binding of plasminogen, plasminogen fragments, tissue plasminogen activator and/or lipoprotein(a) to Plg-$R_{KT}$ and/or immunoreact with Plg-$R_{KT}$ and a Plg-$R_{KT}$ polypeptide of this invention having an amino acid residue sequence represented by the formula selected from the group consisting of: TFESLEKARREQSKLFSDK (SEQ ID NO: 21), GTLLQRMKSEAEDILETEKTK (SEQ ID NO: 22), TEKTKLELPKGLI TFESLEKARR (SEQ ID NO: 23), and KRKKP (SEQ ID NO: 24), but do not immunoreact with the polypeptide having an amino acid residue sequence represented by the formula: AFLVPIVPLSFIFTYQYDLG (SEQ ID NO: 31).

In a related embodiment, the present invention contemplates an antibody comprising antibody molecules that immunoreact with Plg-$R_{KT}$ and a Plg-$R_{KT}$ polypeptide of this invention having an amino acid residue sequence represented by the formula selected from the group consisting of TFESLEKARREQSKLFSDK (SEQ ID NO: 21), GTLLQRMKSEAEDILETEKTK (SEQ ID NO: 22), TEKTKLELPKGLITFESLEKARR (SEQ ID NO: 23), KRKKP (SEQ ID NO: 24), MGFIFSKSMNENMKNQQEFM (SEQ ID NO: 25), NENMKNQQEFMVTHARLQLER (SEQ ID NO: 26), MVTHARLQLERHLTMQNEMRE (SEQ ID NO: 27), and RHLTMQNEMRERQMAMQIAWSRE (SEQ ID NO: 28), ERQMAMQIAWSREFLKYFGTFFG (SEQ ID NO: 29), SREFLKYFGTFFGIATISLATGAL (SEQ ID NO: 30), but do not immunoreact with the polypeptide having an amino acid residue sequence represented by the formula: AFLVPIVPLSFIFTYQYDLG (SEQ ID NO 31).

A method for detecting inflammation, cancer, hematological disorders and maturation of leukocytes in a patient or tissue that comprises detecting the presence of Plg-$R_{KT}$ in body fluid, cells or tissues with an anti-Plg-$R_{KT}$ of this invention.

Further contemplated is a method for identification of plasminogen receptors and a method for identification of cell surface receptors.

DETAILED DESCRIPTION OF THE INVENTION

A. Definitions

Amino Acid Residue: The amino acid residues described herein are preferred to be in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |

-continued

TABLE OF CORRESPONDENCE

| SYMBOL | | |
|---|---|---|
| 1-Letter | 3-Letter | AMINO ACID |
| R | Arg | arginine |
| D | Asp | aspartic acid |
| N | Asn | asparagine |
| C | Cys | cysteine |

It should be noted that all amino acid residue sequences are represented herein by formulas whose left and right orientation is in the conventional direction of amino-terminus to carboxy-terminus. Furthermore, it should be noted that a dash at the beginning or end of an amino acid residue sequence indicates either a peptide bond to a further sequence of one or more amino acid residues or a covalent bond to a carboxyl or hydroxyl end group. The absence of a dash indicates a polypeptide with no additional amino acid residues other than those specified.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between and antigenic determinant-containing molecule and a molecule containing an antibody combining site such as a whole antibody molecule or a portion thereof.

Monoclonal Antibody: The phrase monoclonal antibody in its various grammatical forms refers to a population of antibody molecules that contains only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen, e.g., a bispecific monoclonal antibody.

Lipoprotein(a): a distinct lipoprotein particle with a structure similar to low densitylipoprotein (LDL) but containing an unique apoprotein moiety, [(apolipoprotein(a)], which is disulfide-linked to apoB-100. Apolipoprotein(a) is highly homologous to plasminogen. Lipoprotein(a) competes with plasminogen for binding to cells and is associated with the development of premature atherosclerosis and with disease processes involving thrombosis.

Plasminogen: (PLG; MIME 173350; abbreviation: plg; EC 3.4.21.7; Swissprot P00747; Gene map locus and chromosome position 6q26)(bovine, dog, hedgehog, horse, lamprey, mouse, pig, rat, rhesus monkey, sheep). Precursor of plasmin, a trypsin.like enzyme, that efficiently degrades fibrin and most extracellular matrix proteins, except collagen and elastin. Contains five kringle domains and a serine protease domain. A plasminogen deficiency is linked to ligneous conjunctivitis.

Plasminogen Fragments: Proteolytic digestion products of native plasminogen that contain at least one kringle domain. These plasminogen fragments include angiostatin and other fragments that have angiostatic activity.

Polypeptide and Peptide: Polypeptide and peptide are terms used interchangeably herein to designate a linear series of amino acid residues connected one to the other by peptide bonds between the alpha-amino and carboxy groups of adjacent residues.

Synthetic Peptide: Synthetic Peptide refers to a chemically produced chain of amino acid residues linked together by peptide bonds that is free of naturally occurring proteins and fragments thereof.

Tissue Plasminogen Activator: (PLAT; MIME 173370; abbreviation: t-PA; EC 3.4.21.68; Swissprot P00750; Gene map locus and chromosome position 8p12)(bovine, mouse, rat). Principal substrate is plasminogen, requires a cofactor such as fibrin, extracellular matric proteins or cell surface receptor to activate plasminogen efficiently. Contains a finger domain, a growth factor domain, two kringle domains and a serine protease domain.

B. Polypeptides

As used herein, the phrase "Plg-$R_{KT}$ polypeptide" refers to a polypeptide having an amino acid residue sequence that includes a sequence that corresponds, and preferably is identical, to a portion of the Plg-$R_{KT}$ molecule. The Plg-$R_{KT}$ molecule consists of a 147 amino acid residue single chain. The amino acid residue sequence of murine Plg-$R_{KT}$ is listed as SEQ ID NO:. 1 in the sequence listing.

```
SEQ ID NO: 1:
1MGFIFSKSMNENMKNQQEFMVTHARLQLERHLTMQNEMRERQMAMQIA

WSREFLKYFGTFFGIATISLATGALKRKKPAFLVPIVPLSFIFTYQYDLG

YGTLLQRMKSEAEDILETEKTKLELPKGLITFESLEKARREQSKLFSD

K147
```

In one embodiment, a Plg-$R_{KT}$ polypeptide of the present invention comprises no more than about 50 amino acids, preferably no more than about 45 residues, and includes an amino acid sequence represented by the formula-RMKSE-AEDILETEKTKLELPXGLITFESLE-KARXEQSXLFSDK-(SEQ ID NO: 2) wherein X is either K or R. (The sequence constitutes residues 105 to 147 of Plg-$R_{KT}$ wherein X is either K or R.) This polypeptide defines a conserved native epitope on Plg-$R_{KT}$ and has the capacity to inhibit the binding of plasminogen, plasminogen fragments, tissue plasminogen activator and/or lipoprotein(a) to Plg-$R_{KT}$ according to the teachings herein.

In a related embodiment, a Plg-$R_{KT}$ polypeptide of the present invention comprises no more than about 50 amino acids, preferably no more than about 45 residues, and includes an amino acid sequence represented by the formula RMKSEAEDILETEKTKLELPKGLIT-FESLEKARREQSKLFSDK-(SEQ ID NO: 3). (The sequence constitutes residues 105 to 147 of Plg-$R_{KT}$). This polypeptide defines a conserved native epitope on Plg-$R_{KT}$ and has the capacity to inhibit the binding of plasminogen, plasminogen fragments, tissue plasminogen activator and/or lipoprotein(a) to Plg-$R_{KT}$ according to the teachings herein.

Another related embodiment of the present invention contemplates a Plg-$R_{KT}$ polypeptide that comprises no more than about 50 amino acids, preferably no more than about 45 residues, and includes an amino acid sequence represented by the formula-KSEAEDILETEKTKLELPXGLITFESLE-KARXEQSXLFSDK-, (SEQ ID NO: 4), wherein X is either K or R) (The sequence constitutes residues 107 to 147 of Plg-$R_{KT}$ wherein X is either K or R). This polypeptide defines a conserved native epitope on Plg-$R_{KT}$ and has the capacity to inhibit the binding of plasminogen, plasminogen fragments, tissue plasminogen activator and/or lipoprotein(a) to Plg-$R_{KT}$ according to the teachings herein.

A further related embodiment of the present invention contemplates a Plg-$R_{KT}$ polypeptide of the present invention comprises no more than about 50 amino acids, preferably no more than about 45 residues, and includes an amino acid sequence represented by the formula KSEAEDILETEKT-KLELPKGLITFESLEKARREQSKLFSDK-(SEQ ID NO: 5). (The sequence constitutes residues 107 to 147 of Plg-$R_{KT}$. This polypeptide defines a conserved native epitope on Plg-$R_{KT}$ and has the capacity to inhibit the binding of plasminogen, plasminogen fragments, tissue plasminogen activator and/or lipoprotein(a) to Plg-$R_{KT}$ according to the teachings herein.

Another related embodiment of the present invention contemplates a Plg-$R_{KT}$ polypeptide that comprises no more than about 50 amino acids, preferably no more than about 40 residues, more preferably no more than about 30 residues and includes an amino acid sequence represented by the formula-KTKLELPXGLITFESLEKARXEQSXLFSDK-(SEQ ID NO: 6 wherein X is either K or R). (The sequence constitutes residues 118 to 147 of Plg-$R_{KT}$ wherein X is either K or R). This polypeptide defines a conserved native epitope on Plg-$R_{KT}$ and has the capacity to inhibit the binding of plasminogen, plasminogen fragments, tissue plasminogen activator and/or lipoprotein(a) to Plg-$R_{KT}$ according to the teachings herein.

A further related embodiment of the present invention contemplates a Plg-$R_{KT}$ polypeptide that comprises no more than about 50 amino acids, preferably no more than about 40 residues, more preferably no more than about 30 residues and includes an amino acid sequence represented by the formula-KTKLELPKGLITFESLEKARREQSKLFSDK-(SEQ ID NO: 7) (The sequence constitutes residues 118 to 147 of Plg-$R_{KT}$). This polypeptide defines a conserved native epitope on Plg-$R_{KT}$ and has the capacity to inhibit the binding of plasminogen, plasminogen fragments, tissue plasminogen activator and/or lipoprotein(a) to Plg-$R_{KT}$ according to the teachings herein.

Another related embodiment of the present invention contemplates a Plg-$R_{KT}$ polypeptide that comprises no more than about 50 amino acids, preferably no more than about 40 residues, more preferably no more than about 28 residues and includes an amino acid sequence represented by the formula-KLELPXGLITFESLEKARXEQSXLFSDK-, (SEQ ID NO: 8, wherein X is either K or R). (The sequence constitutes residues 120 to 147 of Plg-$R_{KT}$ wherein X is either K or R). This polypeptide defines a conserved native epitope on Plg-$R_{KT}$ and has the capacity to inhibit the binding of plasminogen, plasminogen fragments, tissue plasminogen activator and/or lipoprotein(a) to Plg-$R_{KT}$ according to the teachings herein.

A further related embodiment of the present invention contemplates a Plg-$R_{KT}$ polypeptide that comprises no more than about 50 amino acids, preferably no more than about 40 residues, more preferably no more than about 30 residues and includes an amino acid sequence represented by the formula-KLELPKGLITFESLEKARREQSKLFSDK-(SEQ ID NO: 9) (The sequence constitutes residues 120 to 147 of Plg-$R_{KT}$.) This polypeptide defines a conserved native epitope on Plg-$R_{KT}$ and has the capacity to inhibit the binding of plasminogen, plasminogen fragments, tissue plasminogen activator and/or lipoprotein(a) to Plg-$R_{KT}$ according to the teachings herein.

Another related embodiment of the present invention contemplates a Plg-$R_{KT}$ polypeptide that comprises no more than about 50 amino acids, preferably no more than about 40 residues, more preferably no more than about 25 residues and includes an amino acid sequence represented by the formula-XGLITFESLEKARXEQSXLFSDK-, (SEQ ID NO: 10, wherein X is either K or R). (The sequence constitutes residues 125 to 147 of Plg-$R_{KT}$ wherein X is either K or R). This polypeptide defines a conserved native epitope on Plg-$R_{KT}$ and has the capacity to inhibit the binding of plasminogen, plasminogen fragments, tissue plasminogen activator and/or lipoprotein(a) to Plg-$R_{KT}$ according to the teachings herein.

A further related embodiment of the present invention contemplates a Plg-$R_{KT}$ polypeptide that comprises no more than about 50 amino acids, preferably no more than about 40 residues, more preferably no more than about 25 residues and includes an amino acid sequence represented by the formula-KGLITFESLEKARREQSKLFSDK-) (SEQ ID NO: 11. (The sequence constitutes residues 125 to 147 of Plg-$R_{KT}$). This polypeptide defines a conserved native epitope on Plg-$R_{KT}$ and has the capacity to inhibit the binding of plasminogen, plasminogen fragments, tissue plasminogen activator and/or lipoprotein(a) to Plg-$R_{KT}$ according to the teachings herein.

Another related embodiment of the present invention contemplates a Plg-$R_{KT}$ polypeptide that comprises no more than about 50 amino acids, preferably no more than about 40 residues, more preferably no more than about 15 residues and includes an amino acid sequence represented by the formula-KARXEQSXLFSDK-(SEQ ID NO: 12, wherein X is either K or R). (The sequence constitutes residues 135 to 147 of Plg-$R_{KT}$ wherein X is either K or R.) This polypeptide defines a conserved native epitope on Plg-$R_{KT}$ and has the capacity to inhibit the binding of plasminogen, plasminogen fragments, tissue plasminogen activator and/or lipoprotein(a) to Plg-$R_{KT}$ according to the teachings herein.

A further related embodiment of the present invention contemplates a Plg-$R_{KT}$ polypeptide that comprises no more than about 50 amino acids, preferably no more than about 40 residues, more preferably no more than about 15 residues and includes an amino acid sequence represented by the formula-KARREQSKLFSDK-(SEQ ID NO: 13, wherein X is either K or R) (The sequence constitutes residues 135 to 147 of Plg-$R_{KT}$). This polypeptide defines a conserved native epitope on Plg-$R_{KT}$ and has the capacity to inhibit the binding of plasminogen, plasminogen fragments, tissue plasminogen activator and/or lipoprotein(a) to Plg-$R_{KT}$ according to the teachings herein.

Another related embodiment of the present invention contemplates a Plg-$R_{KT}$ polypeptide that comprises no more than about 50 amino acids, preferably no more than about 40 residues, more preferably no more than about 12 residues and includes an amino acid sequence represented by the formula-RXEQSXLFSDK-, (SEQ ID NO: 14 wherein X is either K or R). (The sequence constitutes residues 137 to 147 of Plg-$R_{KT}$ wherein X is either K or R.) This polypeptide defines a conserved native epitope on Plg-$R_{KT}$ and has the capacity to inhibit the binding of plasminogen, plasminogen fragments, tissue plasminogen activator and/or lipoprotein(a) to Plg-$R_{KT}$ according to the teachings herein.

A further related embodiment of the present invention contemplates a Plg-$R_{KT}$ polypeptide that comprises no more than about 50 amino acids, preferably no more than about 40 residues, more preferably no more than about 15 residues and includes an amino acid sequence represented by the formula- RREQSKLFSDK-(SEQ ID NO: 15). (The sequence constitutes residues 137 to 147 of Plg-R$_{KT}$). This polypeptide defines a conserved native epitope on Plg-R$_{KT}$ and has the capacity to inhibit the binding of plasminogen, plasminogen fragments, tissue plasminogen activator and/or lipoprotein(a) to Plg-R$_{KT}$ according to the teachings herein.

Another related embodiment of the present invention contemplates a Plg-R$_{KT}$ polypeptide that comprises no more than about 50 amino acids, preferably no more than about 40 residues, more preferably no more than about 12 residues and includes an amino acid sequence represented by the formula XEQSXLFSDK-, (SEQ ID NO: 16 wherein X is either K or R). (The sequence constitutes residues 138 to 147 of Plg-R$_{KT}$ wherein X is either K or R.). This polypeptide defines a conserved native epitope on Plg-R$_{KT}$ and has the capacity to inhibit the binding of plasminogen, plasminogen fragments, tissue plasminogen activator and/or lipoprotein(a) to Plg-R$_{KT}$ according to the teachings herein.

A further related embodiment of the present invention contemplates a Plg-R$_{KT}$ polypeptide that comprises no more than about 50 amino acids, preferably no more than about 40 residues, more preferably no more than about 12 residues and includes an amino acid sequence represented by the formula- REQSKLFSDK-(SEQ ID NO: 17). (The sequence constitutes residues 138 to 147 of Plg-R$_{KT}$). This polypeptide defines a conserved native epitope on Plg-R$_{KT}$ and has the capacity to inhibit the binding of plasminogen, plasminogen fragments, tissue plasminogen activator and/or lipoprotein(a) to Plg-R$_{KT}$ according to the teachings herein.

Another related embodiment of the present invention contemplates a Plg-R$_{KT}$ polypeptide that comprises no more than about 50 amino acids, preferably no more than about 40 residues, more preferably no more than about 10 residues and includes an amino acid sequence represented by the formula- XLFSDK-, (SEQ ID NO: 18 wherein X is either K or R.) (The sequence constitutes residues 142 to 147 of Plg-R$_{KT}$ wherein X is either K or R.). This polypeptide defines a conserved native epitope on Plg-R$_{KT}$ and has the capacity to inhibit the binding of plasminogen, plasminogen fragments, tissue plasminogen activator and/or lipoprotein(a) to Plg-R$_{KT}$ according to the teachings herein.

A further related embodiment of the present invention contemplates a Plg-R$_{KT}$ polypeptide that comprises no more than about 50 amino acids, preferably no more than about 40 residues, more preferably no more than about 12 residues and includes an amino acid sequence represented by the formula; -KLFSDK-(SEQ ID NO: 19). (The sequence constitutes residues 142 to 147 of Plg-R$_{KT}$). This polypeptide defines a conserved native epitope on Plg-R$_{KT}$ and has the capacity to inhibit the binding of plasminogen, plasminogen fragments, tissue plasminogen activator and/or lipoprotein(a) to Plg-R$_{KT}$ according to the teachings herein.

Another related embodiment of the present invention contemplates a Plg-R$_{KT}$ polypeptide that comprises no more than about 50 amino acids, preferably no more than about 40 residues, more preferably no more than about 10 residues and includes an amino acid sequence represented by the formula- LFSDK-, (SEQ ID NO: 20). (The sequence constitutes residues 143 to 147 of Plg-R$_{KT}$). This polypeptide defines a conserved native epitope on Plg-R$_{KT}$ and has the capacity to inhibit the binding of plasminogen, plasminogen fragments, tissue plasminogen activator and/or lipoprotein(a) to Plg-R$_{KT}$ according to the teachings herein.

Preferred Plg-R$_{KT}$ polypeptides, their designations, and their Plg-R$_{KT}$ amino acid residue positions are shown in Table 1.

TABLE 1

Table of Preferred Plg-R$_{KT}$ Polypeptides

| Peptide Sequence | N-terminus residue number | C-terminus residue number |
|---|---|---|
| RMKSEAEDILETEKTKLELPXGLITFESLEKARXEQSXLFSDK[1] (SEQ ID NO: 2) | 105 | 147 |
| RMKSEAEDILETEKTKLELPKGLITFESLEKARREQSKLFSDK* (SEQ ID NO: 3) | 105 | 147 |
| KSEAEDILETEKTKLELPXGLITFESLEKARXEQSXLFSDK[1] (SEQ ID NO: 4) | 107 | 147 |
| KSEAEDILETEKTKLELPKGLITFESLEKARREQSKLFSDK* (SEQ ID NO: 5) | 107 | 147 |
| KTKLELPXGLITFESLEKARXEQSXLFSDK[1] (SEQ ID NO: 6) | 118 | 147 |
| KTKLELPKGLITFESLEKARREQSKLFSDK* (SEQ ID NO: 7) | 118 | 147 |
| KLELPXGLITFESLEKARXEQSXLFSDK[1] (SEQ ID NO: 8) | 120 | 147 |
| KLELPKGLITFESLEKARREQSKLFSDK* (SEQ ID NO: 9) | 120 | 147 |
| XGLITFESLEKARXEQSXLFSDK[1] (SEQ ID NO: 10) | 125 | 147 |
| KGLITFESLEKARREQSKLFSDK* (SEQ ID NO: 11) | 125 | 147 |
| KARXEQSXLFSDK[2] (SEQ ID NO: 12) | 135 | 147 |
| KARREQSKLFSDK* (SEQ ID NO: 13) | 135 | 147 |
| RXEQSXLFSDK[2] (SEQ ID NO: 14) | 137 | 147 |
| RREQSKLFSDK* (SEQ ID NO: 15) | 137 | 147 |
| XEQSXLFSDK[2] (SEQ ID NO: 16) | 138 | 147 |

TABLE 1-continued

Table of Preferred Plg-$R_{KT}$ Polypeptides

| Peptide Sequence | N-terminus residue number | C-terminus residue number |
|---|---|---|
| REQSKLFSDK* (SEQ ID NO: 17) | 138 | 147 |
| XLFSDK[3] (SEQ ID NO: 18) | 142 | 147 |
| KLFSDK* (SEQ ID NO: 19) | 142 | 147 |
| LFSDK* (SEQ ID NO: 20) | 143 | 147 |
| TFESLEKARREQSKLFSDK* (SEQ ID NO: 21) | 129 | 147 |
| GTLLQRMKSEAEDILETEKTK* (SEQ ID NO: 22) | 100 | 120 |
| TEKTKLELPKGLITFESLEKARR* (SEQ ID NO: 23) | 116 | 138 |
| KRKKP* (SEQ ID NO: 24) | 74 | 78 |
| MGFIFSKSMNENMKNQQEFM* (SEQ ID NO: 25) | 1 | 20 |
| NENMKNQQEFMVTHARLQLER* (SEQ ID NO: 26) | 10 | 30 |
| MVTHARLQLERHLTMQNEMRE* (SEQ ID NO: 27) | 20 | 40 |
| RHLTMQNEMRERQMAMQIAWSRE* (SEQ ID NO: 28) | 30 | 52 |
| ERQMAMQIAWSREFLKYFGTFFG* (SEQ ID NO: 29) | 40 | 62 |
| SREFLKYFGTFFGIATISLATGAL* (SEQ ID NO: 30) | 50 | 73 |
| AFLVPIVPLSFIFTYQYDLG* (SEQ ID NO: 31) | 79 | 98 |
| KDSFLKSQEC* (SEQ ID NO: 32) = reverse of SEQ. ID NO: 16 | | |

*murine sequence

[1]consensus sequence wherein X is either K or R; includes R substituted for $K_{125}$, includes K substituted for $R_{138}$; includes R substituted for $K_{142}$; includes R substituted for $K_{125}$ and with K substituted for $R_{138}$; includes R substituted for $K_{125}$ and with R substituted for $K_{142}$; includes R substituted for $K_{125}$ and with K substituted for $R_{138}$ and with R substituted for $K_{142}$;; includes K substituted for $R_{138}$, and with R substituted for $K_{142}$. Also includes sequences corresponding to other mammalian species, e.g. with E substituted for $Q_{105}$; with H substituted for $Q_{105}$; with G substituted for $S_{108}$; with N substituted for $D_{112}$; with S substituted for $T_{120}$; with Q substituted for $E_{122}$; with M substituted for $L_{127}$; with I substituted for $L_{133}$; with F substituted for $L_{143}$ and I substituted for $S_{145}$.

[2]consensus sequence wherein X is either K or R; includes K substituted for $R_{138}$; includes R substituted for $K_{142}$; K substituted for $R_{138}$, and with R substituted for $K_{142}$, also includes C substituted for $R_{138}$. Also includes sequences corresponding to other mammalian species, e.g. with F substituted for $L_{143}$ and I substituted for $S_{145}$.

[3]consensus sequence wherein X is either K or R; includes R substituted for $K_{142}$. Also includes sequences corresponding to other mammalian species, e.g. with I substituted for $S_{145}$.

Preferably, a Plg-$R_{KT}$ polypeptide of this invention is further characterized by its ability to immunologically mimic an epitope (antigenic determinant) expressed by Plg-$R_{KT}$.

As used herein, the phrase "immunologically mimic" in its various grammatical forms refers to the ability of a Plg-$R_{KT}$ polypeptide of this invention to immunoreact with an antibody of the present invention that immunoreacts with a native epitope of Plg-$R_{KT}$ as defined herein.

It should be understood that a subject polypeptide need not be identical to the amino acid residue sequence of Plg-$R_{KT}$, so long as it includes the required sequence and is able to inhibit the binding of plasminogen, plasminogen fragments, tissue plasminogen activator or lipoprotein(a) to Plg-$R_{KT}$ in an assay for inhibition of plasminogen, plasminogen fragments, tissue plasminogen activator or lipoprotein(a) binding to Plg-$R_{KT}$ as is described herein.

A subject polypeptide includes any analog, fragment or chemical derivative of a polypeptide whose amino acid residue sequence is shown herein so long as the polypeptide is capable of inhibiting the binding of plasminogen, plasminogen fragments, tissue plasminogen activator or lipoprotein(a) to Plg-$R_{KT}$. Therefore, a present polypeptide can be subject to various changes, substitutions, insertions, and deletions where such changes provide for certain advantages in its use. In this regard, a Plg-$R_{KT}$ polypeptide of this invention corresponds to, rather than is identical to, the sequence of Plg-$R_{KT}$ where one or more changes are made and it retains the ability to inhibit the binding of plasminogen, plasminogen fragments, tissue plasminogen activator or lipoprotein(a) to Plg-$R_{KT}$ in one or more of the assays defined herein for determining the ability to inhibit plasminogen, plasminogen fragments, tissue plasminogen activator or lipoprotein(a) binding to Plg-$R_{KT}$.

The term "analog" includes any polypeptide having an amino acid residue sequence substantially identical to a sequence specifically shown herein in which one or more residues have been conservatively substituted with a functionally similar residue and which displays the ability to inhibit the binding of plasminogen, plasminogen fragments, tissue plasminogen activator or lipoprotein(a) to Plg-$R_{KT}$ as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite inhibition activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

A polypeptide is free of homoserine lactone when there is no detectable homoserine lactone present in the polypeptide when subjected to conventional amino acid analysis able to indicate the presence of homoserine lactone or other amino acids. Amino acid analysis methods suitable to detect homoserine lactone are generally well known in the art.

The term "fragment" refers to any subject polypeptide having an amino acid residue sequence shorter than that of a polypeptide whose amino acid residue sequence is shown herein.

When a polypeptide of the present invention has a sequence that is not identical to the sequence of Plg-$R_{KT}$, it is typically because one or more conservative or non-conservative substitutions have been made, usually no more than about 30 number percent, and preferably no more than 10 number percent of the amino acid residues are substituted. Additional residues may also be added at either terminus of a Plg-$R_{KT}$ polypeptide for the purpose of providing a "linker" by which the polypeptides of this invention can be conveniently affixed to a label or solid matrix, or carrier. Preferably, the linker residues do not form Plg-$R_{KT}$ epitopes, i.e., are not similar in structure to Plg-$R_{KT}$.

Labels, solid matrices and carriers that can be used with the polypeptides of this invention are described hereinbelow.

Amino acid residue linkers are usually at least one residue and can be 40 or more residues, more often 1 to 10 residues, but do not form Plg-$R_{KT}$ epitopes. Typical amino acid residues used for linking are tyrosine, cysteine, lysine, glutamic and aspartic acid, or the like. In addition, a subject polypeptide can differ, unless otherwise specified, from the natural sequence of Plg-$R_{KT}$ by the sequence being modified by terminal-$NH_2$ acylation, e.g., acetylation, or thioglycolic acid amidation, by terminal-carboxlyamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification.

When coupled to a carrier to form what is known in the art as a carrier-hapten conjugate, a Plg-$R_{KT}$ polypeptide of the present invention is capable of inducing antibodies that immunoreact with Plg-$R_{KT}$. In view of the well established principle of immunologic cross-reactivity, the present invention therefore contemplates antigenically related variants of the polypeptides shown in Table 1 above and Table 2 in Examples. An "antigenically related variant" is a subject polypeptide that is capable of inducing antibody molecules that immunoreact with a polypeptide from Table 1 above and from Plg-$R_{KT}$.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

A Plg-$R_{KT}$ polypeptide of the present invention also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W.H. Freeman Co., San Francisco, 1969; M. Bodanszky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

A Plg-$R_{KT}$ polypeptide can also be used to prepare an inoculum as described herein for the preparation of antibodies that immunoreact with epitopes on Plg-$R_{KT}$. A Plg-$R_{KT}$ polypeptide of this invention can also be used in the therapeutic methods of the present invention to inhibit the binding of plasminogen, plasminogen fragments, tissue plasminogen activator or lipoprotein(a) to Plg-$R_{KT}$.

C. Antibodies and Monoclonal Antibodies

The term "antibody" in its various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab')$_2$ portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

In one embodiment, an antibody of the present invention, i.e., an anti-Plg-$R_{KT}$ antibody, comprises antibody molecules that inhibit the binding of plasminogen, plasminogen fragments, tissue plasminogen activator or lipoprotein(a) to Plg-$R_{KT}$ as described herein.

An anti-Plg-$R_{KT}$ antibody is further characterized as being capable of immunoreacting with 1) isolated Plg-$R_{KT}$, and 2) a Plg-$R_{KT}$ polypeptide of the present invention. A preferred antibody is substantially free of antibody molecules that immunoreact with the polypeptide: AFLVPIVPLSFIFTYQYDLG (SEQ ID NO: 31).

In preferred embodiments, an anti-Plg-$R_{KT}$ antibody is characterized as being capable of immunoreacting with a polypeptide having an amino acid residue sequence represented by the formula selected from the group consisting of a polypeptide having an amino acid residue sequence represented by the formula selected from the group consisting of: TFESLEKARREQSKLFSDK (SEQ ID NO: 21), GTLLQRMKSEAEDILETEKTK (SEQ ID NO: 22), TEKTKLELPKGLITFESLEKARR (SEQ ID NO: 23), KRKKP (SEQ ID NO: 24), MGFIFSKSMNENMKNQQEFM (SEQ ID NO: 25), NENMKNQQEFMVTHARLQLER (SEQ ID NO: 26), MVTHARLQLERHLTMQNEMRE (SEQ ID NO: 27), and RHLTMQNEMRERQMAMQIAWSRE (SEQ ID NO: 28), ERQMAMQIAWSREFLKYFGTFFG (SEQ ID NO: 29), SREFLKYFGTFFGIATISLATGAL (SEQ ID NO: 30), but do not immunoreact with the polypeptide having an amino acid residue sequence represented by the formula: AFLVPIVPLSFIFTYQYDLG (SEQ ID NO: 31).

Particularly preferred anti-Plg-$R_{KT}$ antibodies immunoreact with a Plg-$R_{KT}$ polypeptide having a sequence that includes the epitope defined by the formula: -XLFSDK-, (SEQ ID No. 18). Most preferred are anti-Plg-$R_{KT}$ antibodies that immunoreact with the polypeptide having the sequence LFSDK (SEQ ID NO: 20).

Antibody immunoreactivity with Plg-$R_{KT}$-containing antigens can be measured by a variety of immunological assays known in the art. Exemplary immunoreaction of an anti-Plg-$R_{KT}$ antibody with a Plg-$R_{KT}$-peptide is described in Examples 5, 6 and 7. Direct binding with Plg-$R_{KT}$, and with Plg-$R_{KT}$ polypeptides can be assayed at least by the methods described in Example 7.

By "substantially free" means that the antibody molecules do not immunoreact with the stated antigen at levels within one order of magnitude, and preferably within two orders of magnitude, of the levels of positive immunoreacting species of antigen.

An antibody of the present invention is typically produced by immunizing a mammal with an inoculum containing a Plg-$R_{KT}$ polypeptide of this invention and thereby induce in the mammal antibody molecules having immunospecificity for Plg-$R_{KT}$ polypeptide. The antibody molecules are then collected from the mammal and isolated to the extent desired by well known techniques such as, for example, by using DEAE Sephadex to obtain the IgG fraction. Exemplary antibody preparation methods are described herein at Examples 5 and 7.

The preparation of antibodies against polypeptide is well known in the art. [See Staudt et al., *J. Exp. Med.,* 157:687-704 (1983)]. Briefly, to produce a peptide antibody composition of this invention, a laboratory mammal is inoculated with an immunologically effective amount of a Plg-$R_{KT}$ polypeptide homolog, typically as present in a vaccine of the present invention. The anti-Plg-$R_{KT}$ peptide antibody molecules thereby induced are then collected from the mammal and those immunospecific for both the Plg-$R_{KT}$ polypeptide are isolated to the extent desired by well known techniques such as, for example, by immunoaffinity chromatography.

To enhance the specificity of the antibody, the antibodies may be purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

The word "inoculum" in its various grammatical forms is used herein to describe a composition containing a Plg-$R_{KT}$ polypeptide of this invention as an active ingredient used for the preparation of antibodies against a Plg-$R_{KT}$ polypeptide. When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, di-aldehydes such as glutaraldehyde, Klipstein, et al., *J. Infect. Dis.*, 147:318-326 (1983) and the like, or the use of carbodiimide technology as in the use of a water-soluble carbodiimide to form amide links to the carrier. For a review of protein conjugation or coupling through activated functional groups, see Aurameas, et al., *Scand. J. Immunol.*, 1:7-23 (1978). Alternatively, the heterobifunctional cross-linker SPDP (N-succinimidyl-3-(2-pyridyldithio) proprionate)) can be used to conjugate peptides, in which a carboxy-terminal cysteine has been introduced.

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen as is well known in the art. Inocula typically contain polypeptide concentrations of about 10 micrograms to about 500 milligrams per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

The techniques of polypeptide conjugation or coupling through activated functional groups presently known in the art are particularly applicable. See, for example, Aurameas, et al., *Scand. J. Immunol.*, Vol. 8, Suppl. 7:7-23 (1978) and U.S. Pat. No. 4,493,795, No. 3,791,932 and No. 3,839,153. In addition, a site directed coupling reaction can be carried out so that any loss of activity due to polypeptide orientation after coupling can be minimized. See, for example, Rodwell et al., *Biotech.*, 3:889-894 (1985), and U.S. Pat. No. 4,671,958.

One or more additional amino acid residues may be added to the amino- or carboxy-termini of the polypeptide to assist in binding the polypeptide to form a conjugate. Cysteine residues, usually added at the carboxy-terminus of the polypeptide, have been found to be particularly useful for forming conjugates via disulfide bonds, but other methods well-known in the art for preparing conjugates may be used.

Anti-Plg-$R_{KT}$ antibody of this invention can also be used in the therapeutic methods of the present invention to inhibit the binding of plasminogen, plasminogen fragments, tissue plasminogen activator or lipoprotein(a) to Plg-$R_{KT}$.

A preferred anti-Plg-$R_{KT}$ antibody is a monoclonal antibody and is used herein as exemplary of an anti-Plg-$R_{KT}$ antibody.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

A monoclonal antibody of this invention comprises antibody molecules that inhibit the binding of plasminogen, plasminogen fragments, tissue plasminogen activator or lipoprotein(a) to Plg-$R_{KT}$ as described herein. A monoclonal antibody of this invention is further characterized as being capable of immunoreacting with 1) isolated Plg-$R_{KT}$, and 2) a Plg-$R_{KT}$ polypeptide of the present invention as described for the anti-Plg-$R_{KT}$ antibodies of this invention.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, *Nature* 256:495-497 (1975), which description is incorporated by reference. The hybridoma supernates so prepared can be screened for the presence of antibody molecules that immunoreact with a Plg-$R_{KT}$ polypeptide, or for inhibition of the binding of plasminogen, plasminogen fragments, tissue plasminogen activator or lipoprotein(a) to Plg-$R_{KT}$ as described further herein.

Briefly, to form the hybridoma from which the monoclonal antibody composition is produced, a myeloma or other self-perpetuating cell line is fused with lymphocytes obtained from the spleen of a mammal hyperimmunized with a Plg-$R_{KT}$ antigen, such as is present in a Plg-$R_{KT}$-containing lipoprotein particle, or with a Plg-$R_{KT}$ polypeptide of this invention. The polypeptide-induced hybridoma technology is described by Niman et al., *Proc. Natl. Acad. Sci., U.S.A.*, 80:4949-4953 (1983), which description is incorporated herein by reference.

It is preferred that the myeloma cell line used to prepare a hybridoma be from the same species as the lymphocytes. Typically, a mouse of the strain 129 GlX$^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the radioimmunoassay (RIA) and the enzyme linked immunosorbent assay (ELISA) described in Example 7.

A monoclonal antibody of the present invention can also be produced by initiating a monoclonal hybridoma culture comprising a nutrient medium containing a hybridoma that secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

The monoclonal antibodies of this invention can be used in the same manner as disclosed herein for antibodies of the present invention.

For example, the monoclonal antibody can be used in the therapeutic, diagnostic or in vitro methods disclosed herein where inhibition of activated protein C is desired.

Other methods of producing a monoclonal antibody, a hybridoma cell, or a hybridoma cell culture are also well known. See, for example, the method of isolating monoclonal antibodies from an immunological repertoire as described by Sastry, et al., *Proc. Natl. Acad. Sci. USA*, 86:5728-5732 (1989); and Huse et al., *Science*, 246:1275-1281 (1981).

Also contemplated by this invention is the hybridoma cell, and cultures containing a hybridoma cell that produce a monoclonal antibody of this invention.

D. Diagnostic Systems

In another embodiment, a diagnostic system is contemplated for assaying for the presence of a Plg-R$_{KT}$ polypeptide or anti-Plg-R$_{KT}$ antibody in a body fluid, tissue or cell sample such as for monitoring the fate of therapeutically administered Plg-R$_{KT}$ polypeptide or anti-Plg-R$_{KT}$ antibody. The system includes, in an amount sufficient for at least one assay, a subject Plg-R$_{KT}$ polypeptide and/or a subject antibody as a separately packaged immunochemical reagent.

Instructions for use of the packaged reagent are also typically included.

As used herein, the term "package" refers to a solid matrix or material such as glass, plastic, paper, foil and the like capable of holding within fixed limits a polypeptide, polyclonal antibody or monoclonal antibody of the present invention. Thus, for example, a package can be a glass vial used to contain milligram quantities of a contemplated polypeptide or antibody or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In embodiments for detecting a subject Plg-R$_{KT}$ polypeptide or an anti-Plg-R$_{KT}$ antibody in a body fluid, a diagnostic system of the present invention can include a label or indicating means capable of signaling the formation of an immunocomplex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189-231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}$I, $^{125}$I, $^{128}$I, $^{132}$I, and a $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such $^{111}$ indium of $^{3}$H.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3-46 (1981). The techniques of protein conjugation or coupling through activated functional groups are particularly applicable. See, for example, Aurameas, et al., *Scand. J. Immunol.*, Vol. 8 Suppl. 7:7-23 (1978), Rodwell et al., *Biotech.*, 3:889-894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of Plg-$R_{KT}$ polypeptide in a body fluid, of this invention in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; No. 3,850,752; and No. 4,016,043, which are all incorporated herein by reference.

Thus, in some embodiments, a Plg-$R_{KT}$ polypeptide or a monoclonal antibody of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides well known to those skilled in the art, can be used.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

The term "package" refers to a solid matrix or material such as glass, plastic (e.g., polyethylene, polypropylene and polycarbonate), paper, foil and the like capable of holding within fixed limits a diagnostic reagent such as a polypeptide, antibody or monoclonal antibody of the present invention. Thus, for example, a package can be a bottle, vial, plastic and plastic-foil laminated envelope or the like container used to contain a contemplated diagnostic reagent or it can be a microtiter plate well to which microgram quantities of a contemplated diagnostic reagent have been operatively affixed, i.e., linked so as to be capable of being immunologically bound by an antibody or polypeptide to be detected.

A preferred embodiment of the current invention contemplates a method for detecting inflammation in a patient comprising detecting the presence of Plg-$R_{KT}$ with an antibody according to claims 23 and 24. The method uses the diagnostic methods described above and the assay methods described below after collecting a body fluid, tissue or cell sample. Examples in this connection are blood, especially peripheral blood such as venous or arterial blood, portal blood or blood from a central venous catheter (CVC), lymph, urine, exudates, transudates, spinal fluid, seminal fluid, saliva, fluids from natural or unnatural body cavities, bone marrow and dispersed body tissue. The fluids from natural body cavities may be for example serous fluids such as peritoneal and pleural fluids, and the fluids from unnatural body cavities may be for example fluids from cysts, vascular fluid, lymphatic fluid or urine sample. Because differentiation of monocytes to macrophages increases Plg-$R_{KT}$ expression, and inflammation is accompanied by increased differentiation of monocytes, increased expression of Plg-$R_{KT}$ should reflect the presence of inflammation in a patient.

A related embodiment of the current invention contemplates a method for detecting inflammation in a tissue (blood or tissue sample) comprising detecting the presence of Plg-$R_{KT}$ with an antibody according to claims 23 and 24. The method uses the diagnostic methods described above and the assay methods described below after collecting a body fluid, tissue or cell sample. Examples in this connection are blood, especially peripheral blood such as venous or arterial blood, portal blood or blood from a central venous catheter (CVC), lymph, urine, exudates, transudates, spinal fluid, seminal fluid, saliva, fluids from natural or unnatural body cavities, bone marrow and dispersed body tissue. The fluids from natural body cavities may be for example serous fluids such as peritoneal and pleural fluids, and the fluids from unnatural body cavities may be for example fluids from cysts, vascular fluid, lymphatic fluid or urine sample. Because differentiation of monocytes to macrophages increases Plg-$R_{KT}$ expression, and inflammation is accompanied by increased differentiation of monocytes, increased expression of Plg-$R_{KT}$ should reflect inflammation in a tissue.

A preferred embodiment of the current invention contemplates a method for detecting cancer in a patient comprising detecting the presence of Plg-$R_{KT}$ with an antibody according to claims 23 and 24. The method uses the diagnostic methods described above and the assay methods described below after collecting a body fluid, tissue or cell sample. Examples in this connection are blood, especially peripheral blood such as venous or arterial blood, portal blood or blood from a central venous catheter (CVC), lymph, urine, exudates, transudates, spinal fluid, seminal fluid, saliva, fluids from natural or unnatural body cavities, bone marrow and dispersed body tissue. The fluids from natural body cavities may be for example serous fluids such as peritoneal and pleural fluids, and the fluids from unnatural body cavities may be for example fluids from cysts, vascular fluid, lymphatic fluid or urine sample. Because $Plg-R_{KT}$ expression is observed on breast cancer and other lymphoid cancers, for example, increased expression of $Plg-R_{KT}$ should reflect the presence of cancer in a patient. Detection of the expression of tumor markers, such as, for example, that of $Plg-R_{KT}$ expression in the enriched cells, can be employed directly as tumor marker. In staging investigations it is possible to correlate the number of detected disseminated tumor cells with the clinical picture, and establish an individual tumor staging. After removal of the primary tumor, the patient can undergo regular checks for recurrence and be immediately treated if there is a positive finding. Further possible uses are the detection of residual tumor cells in the bone marrow of patients who must undergo high-dose radiotherapy, or of disseminated tumor cells within the framework of new therapeutic approaches, and ex vivo and in vivo gene therapeutic approaches.

A related embodiment of the current invention contemplates a method for detecting cancer in a tissue (blood or tissue sample) comprising detecting the presence of $Plg-R_{KT}$ with an antibody according to claims 23 and 24. The method uses the diagnostic methods described above and the assay methods described below after collecting a body fluid, tissue or cell sample. Examples in this connection are blood, especially peripheral blood such as venous or arterial blood, portal blood or blood from a central venous catheter (CVC), lymph, urine, exudates, transudates, spinal fluid, seminal fluid, saliva, fluids from natural or unnatural body cavities, bone marrow and dispersed body tissue. The fluids from natural body cavities may be for example serous fluids such as peritoneal and pleural fluids, and the fluids from unnatural body cavities may be for example fluids from cysts, vascular fluid, lymphatic fluid or urine sample. Because $Plg-R_{KT}$ expression is observed on breast cancer and other lymphoid cancers, for example, increased expression of $Plg-R_{KT}$ should reflect increased risk for cancer in a patient.

A preferred embodiment of the current invention contemplates a method for identifying patients at risk for cancer comprising detecting the presence of $Plg-R_{KT}$ with an antibody according to claims 23 and 24. The method uses the diagnostic methods described above and the assay methods described below after collecting a body fluid, tissue or cell sample. Examples in this connection are blood, especially peripheral blood such as venous or arterial blood, portal blood or blood from a central venous catheter (CVC), lymph, urine, exudates, transudates, spinal fluid, seminal fluid, saliva, fluids from natural or unnatural body cavities, bone marrow and dispersed body tissue. The fluids from natural body cavities may be for example serous fluids such as peritoneal and pleural fluids, and the fluids from unnatural body cavities may be for example fluids from cysts, vascular fluid, lymphatic fluid or urine sample. Because $Plg-R_{KT}$ expression is observed on breast cancer and other lymphoid cancers, for example, increased expression of $Plg-R_{KT}$ should reflect increased risk for cancer in a patient.

A related embodiment of the current invention contemplates a method for identifying patients at risk for metastasis comprising detecting the presence of $Plg-R_{KT}$ with an antibody according to claims 23 and 24. The method uses the diagnostic methods described above and the assay methods described below after collecting a body fluid, tissue or cell sample. Examples in this connection are blood, especially peripheral blood such as venous or arterial blood, portal blood or blood from a central venous catheter (CVC), lymph, urine, exudates, transudates, spinal fluid, seminal fluid, saliva, fluids from natural or unnatural body cavities, bone marrow and dispersed body tissue. The fluids from natural body cavities may be for example serous fluids such as peritoneal and pleural fluids, and the fluids from unnatural body cavities may be for example fluids from cysts, vascular fluid, lymphatic fluid or urine sample. Because $Plg-R_{KT}$ expression is observed on breast cancer and other lymphoid cancers, for example, increased expression of $Plg-R_{KT}$ should reflect increased risk for metastasis in a patient. Detection of the expression of tumor markers, such as, for example, that of $Plg-R_{KT}$ expression in the enriched cells, can be employed directly as tumor marker. In staging investigations it is possible to correlate the number of detected disseminated tumor cells with the clinical picture, and establish an individual tumor staging. After removal of the primary tumor, the patient can undergo regular checks for recurrence and be immediately treated if there is a positive finding. Further possible uses are the detection of residual tumor cells in the bone marrow of patients who must undergo high-dose radiotherapy, or of disseminated tumor cells within the framework of new therapeutic approaches, and ex vivo and in vivo gene therapeutic approaches.

A preferred embodiment of the current invention contemplates a method for detecting hematologic disorders in a patient comprising detecting the presence of $Plg-R_{KT}$ with an antibody according to claims 23 and 24. The method uses the diagnostic methods described above and the assay methods described below after collecting a body fluid, tissue or cell sample. Examples in this connection are blood, especially peripheral blood such as venous or arterial blood, portal blood or blood from a central venous catheter (CVC), lymph, urine, exudates, transudates, spinal fluid, seminal fluid, saliva, fluids from natural or unnatural body cavities, bone marrow and dispersed body tissue. The fluids from natural body cavities may be for example serous fluids such as peritoneal and pleural fluids, and the fluids from unnatural body cavities may be for example fluids from cysts, vascular fluid, lymphatic fluid or urine sample. Because $Plg-R_{KT}$ expression is observed on leukocytes, including monocytes, T cells, NK cells and myeloid cells, increased $Plg-R_{KT}$ expression should reflect the presence of hematologic disorders, such as HIV or other immunodeficiencies, chronic granulomatous disease, Krabbe disease, neutropenia and leukemias in a patient.

A related embodiment of the current invention contemplates a method for detecting hematologic disorders in a tissue (blood or tissue sample) comprising detecting the presence of $Plg-R_{KT}$ with an antibody according to claims 23 and 24. The method uses the diagnostic methods described above and the assay methods described below after collecting a body fluid, tissue or cell sample. Examples in this connection are blood, especially peripheral blood such as venous or arterial blood, portal blood or blood from a central venous catheter (CVC), lymph, urine, exudates, transudates, spinal fluid, seminal fluid, saliva, fluids from natural or unnatural body cavities, bone marrow and dispersed body tissue. The fluids from natural body cavities may be for example serous fluids such as peritoneal and pleural fluids, and the fluids from unnatural body cavities may be for example fluids from cysts, vascular fluid, lymphatic fluid or urine sample. Because $Plg-R_{KT}$ expression is observed on leukocytes, including monocytes, T cells, NK cells and myeloid cells, increased $Plg-R_{KT}$ expression should reflect the presence of hematologic disorders, such as HIV or other immunodeficiencies, chronic granulomatous disease, Krabbe disease, neutropenia and leukemias in a tissue.

A preferred embodiment of the current invention contemplates a method for detecting maturation of leukocytes in a patient comprising detecting the presence of Plg-$R_{KT}$ with an antibody according to claims 23 and 24. The method uses the diagnostic methods described above and the assay methods described below after collecting a body fluid, tissue or cell sample. Examples in this connection are blood, especially peripheral blood such as venous or arterial blood, portal blood or blood from a central venous catheter (CVC), lymph, urine, exudates, transudates, spinal fluid, seminal fluid, saliva, fluids from natural or unnatural body cavities, bone marrow and dispersed body tissue. The fluids from natural body cavities may be for example serous fluids such as peritoneal and pleural fluids, and the fluids from unnatural body cavities may be for example fluids from cysts, vascular fluid, lymphatic fluid or urine sample. Because Plg-$R_{KT}$ expression increases when leukocytes differentiate, increased Plg-$R_{KT}$ expression should provide a marker for leukocyte differentiation. This would be useful in following the success of bone marrow transplants, for example.

A related embodiment of the current invention contemplates a method for detecting maturation of leukocytes in a tissue (blood or tissue sample) comprising detecting the presence of Plg-$R_{KT}$ with an antibody according to claims 23 and 24. The method uses the diagnostic methods described above and the assay methods described below after collecting a body fluid, tissue or cell sample. Examples in this connection are blood, especially peripheral blood such as venous or arterial blood, portal blood or blood from a central venous catheter (CVC), lymph, urine, exudates, transudates, spinal fluid, seminal fluid, saliva, fluids from natural or unnatural body cavities, bone marrow and dispersed body tissue. The fluids from natural body cavities may be for example serous fluids such as peritoneal and pleural fluids, and the fluids from unnatural body cavities may be for example fluids from cysts, vascular fluid, lymphatic fluid or urine sample. Because Plg-$R_{KT}$ expression increases when leukocytes differentiate, increased Plg-$R_{KT}$ expression should provide a marker for leukocyte differentiation. This would be useful in following the success of bone marrow transplants, for example.

E. Assay Methods

The present invention contemplates various immunoassay methods for determining the presence, and preferably the amount, of Plg-$R_{KT}$ of the present invention in a body fluid sample using a polypeptide, polyclonal antibody or monoclonal antibody of this invention as an immunochemical reagent to form an immunoreaction product whose amount relates, either directly or indirectly, to the amount of the Plg-$R_{KT}$ in the sample. This embodiment is particularly useful to monitor the fate of therapeutically administered Plg-$R_{KT}$ as described in the therapeutic methods herein.

Those skilled in the art will understand that there are numerous well known clinical diagnostic chemistry procedures in which an immunochemical reagent of this invention can be used to form an immunoreaction product whose amount relates to the amount of Plg-$R_{KT}$ present in a body sample. Thus, while exemplary assay methods are described herein, the invention is not so limited.

Various heterogenous and homogeneous protocols, either competitive or noncompetitive, can be employed in performing an assay method of this invention. Typically, the present assay method comprises the steps of:

(a) Forming an immunoreaction admixture by admixing a human or animal body fluid. Examples in this connection are blood, especially peripheral blood such as venous or arterial blood, portal blood or blood from a central venous catheter (CVC), lymph, urine, exudates, transudates, spinal fluid, seminal fluid, saliva, fluids from natural or unnatural body cavities, bone marrow and dispersed body tissue. The fluids from natural body cavities may be for example serous fluids such as peritoneal and pleural fluids, and the fluids from unnatural body cavities may be for example fluids from cysts, vascular fluid, lymphatic fluid or urine sample with an anti-Plg-$R_{KT}$ antibody of the present invention, preferably a monoclonal antibody, or a Plg-$R_{KT}$ polypeptide of the present invention. Where the fluid sample contains a Plg-$R_{KT}$ polypeptide, an anti-Plg-$R_{KT}$ antibody immunospecific for the Plg-$R_{KT}$ polypeptide is added to form the immunoreaction admixture. Where the fluid sample contains an anti-Plg-$R_{KT}$ antibody, a Plg-$R_{KT}$ polypeptide is added to form the immunoreaction admixture.

Preferably, the fluid sample is provided as a known amount of blood, or a blood derived product such as serum or plasma, or lymphatic fluid or urine sample.

Preferably, the amount of antibody or lymphatic fluid or urine sample polypeptide as immunochemical reagent that is admixed is known. Further preferred are embodiments where the antibody is labeled, i.e., operatively linked to an indicating means such as an enzyme, radionuclide and the like.

In preferred embodiments, the immunochemical reagent is present as part of a solid support, i.e., operatively linked to a solid matrix, so that the immunoreaction admixture formed has a solid and a liquid phase and the immunochemical reagent functions as a capture reagent. Further preferred are embodiments wherein the amount of polypeptide present in the immunoreaction admixture is an amount sufficient to form an excess of epitopes relative to the number of antibody combining sites present in the immunoreaction admixture capable of immunoreacting with those epitopes.

(b) The immunoreaction admixture is maintained under biological assay conditions for a predetermined time period such as about 10 minutes to about 16-20 hours at a temperature of about 4 degrees C. to about 45 degrees C. that, such time being sufficient for the Plg-$R_{KT}$ polypeptide present in the sample to immunoreact with (immunologically bind) the immunochemical reagent to form an Plg-$R_{KT}$ polypeptide-containing immunoreaction product (immunocomplex). In embodiments where the immunochemical reagent is in the solid phase, the immunocomplex formed is also present in the solid phase.

Biological assay conditions are those that maintain the biological activity of the immunochemical reagents of this invention and the Plg-$R_{KT}$ polypeptide sought to be assayed. Those conditions include a temperature range of about 4 degrees C. to about 45 degrees C., a pH value range of about 5 to about 9 and an ionic strength varying from that of distilled water to that of about one molar sodium chloride. Methods for optimizing such conditions are well known in the art.

(c) The amount of Plg-$R_{KT}$ polypeptide-containing immunoreaction product that formed in step (b) is determined, thereby determining the amount of Plg-$R_{KT}$ polypeptide present in the sample.

Determining the amount of the Plg-$R_{KT}$ polypeptide-containing immunoreaction product, either directly or indirectly, can be accomplished by assay techniques well known in the art, and typically depend on the type of indicating means used.

In preferred competitive assay methods, the amount of product determined in step (c) is related to the amount of immunoreaction product similarly formed and determined using a control sample in place of the vascular fluid sample, wherein the control sample contains a known amount of a subject polypeptide or antibody from which a standard curve is determined.

Exemplary of the contemplated diagnostic assay, wherein a Plg-$R_{KT}$ polypeptide is operatively linked to a solid matrix is the ELISA described in Examples 4 and 7.

Also contemplated are immunological assays capable of detecting the presence of immunoreaction product formation without the use of a label. Such methods employ a "detection means", which means are themselves well-known in clinical diagnostic chemistry and constitute a part of this invention only insofar as they are utilized with otherwise novel polypeptides, methods and systems. Exemplary detection means include methods known as biosensors and include biosensing methods based on detecting changes in the reflectivity of a surface, changes in the absorption of an evanescent wave by optical fibers or changes in the propagation of surface acoustical waves.

The present invention contemplates various immunoassay methods for determining the presence, and preferably the amount, of Plg-$R_{KT}$ of the present invention on cells from a body fluid sample using a polypeptide, polyclonal antibody or monoclonal antibody of this invention as an immunochemical reagent to form an immunoreaction product whose amount relates, either directly or indirectly, to the amount of the Plg-$R_{KT}$ in the sample.

The body fluid to be investigated is taken or collected, in accordance with conventional standard protocols. Depending on the nature of the body fluid, it is then either firstly diluted with a diluent, preferably a buffer, or layered directly, undiluted, over the cell separation medium in a closable centrifugation vessel. Alternatively, the body fluid can previously be centrifuged at, for example, 1 000.times.g for about 10 minutes and, after resuspension of the cells in a buffer, layered over the cell separation medium. The buffer which is preferably used is Dulbecco's PBS. The centrifugation is advantageously carried out at about 500 to 2 000.times.g, preferably at about 1 000.times.g, for about 10 to 30 minutes, preferably for 20-30 minutes. The temperature during the centrifugation is preferably about 4° C. The effect of this that catalytic activity of proteases, DNAses and RNAses is minimized.

The cell separation medium which can be used is in principle any suitable fluid of desired density. The density is in the range from 1.055 to 1.065 g/ml, preferably in the range from 1.059 to 1.062 g/ml and is most preferably 1.060.+-.0.0005 g/ml. The density in a particular embodiment is less than 1.065 g/ml, i.e. from 1.055 to <1.065 g/ml. The cell separation medium ought not to react with the body fluid or the cells present therein. It is advantageously possible for example to use Ficoll.RTM. (high mass polysaccharide that dissolves in aqueous solutions) or Percoll.RTM., (medium containing colloidal silica particles coated with polyvinylpyrrolidone) or a Percoll- or Ficoll.RTM.-like medium, with the solutions in each case being brought to the desired density in accordance with the manufacturer's instructions. The density of the cell separation medium is advantageously adjusted with the aid of density meter at the appropriate working temperature of 4 degree C. The cell separation medium may comprise a dye which makes the cell separation medium distinguishable in color from the overlying body fluid, and thus simplifies location of the interphase.

The present invention contemplates various immunoassay methods for determining the presence, and preferably the amount, of Plg-$R_{KT}$ of the present invention in a body tissue sample using a polypeptide, polyclonal antibody or monoclonal antibody of this invention as an immunochemical reagent to form an immunoreaction product whose amount relates, either directly or indirectly, to the amount of the Plg-$R_{KT}$ in the sample.

The methods for detecting expression of Plg-$R_{KT}$ encompass the whole range of conventional diagnostic methods. Examples thereof are microscopic, immuno-cytological/immunocytochemical, biochemical and/or molecular biological methods. It is possible for example to detect the expression of Plg-$R_{KT}$ after enrichment directly or after cell culture and expansion of the cells by morphological, immunocytological/immunocytochemical, biochemical and/or molecular biological methods.

In one embodiment, determination of whether the enriched cells express Plg-$R_{KT}$ includes reverse transcription of mRNA from the enriched cells, and carrying out a PCR with at least one primer specific for Plg-$R_{KT}$. In another embodiment, the enriched cells are brought into contact with a monoclonal or polyclonal antibody that is specific for Plg-$R_{KT}$ and subsequently antibody bound to the cells is detected. These methods can be carried out in single or combination analysis.

Examples of direct detection methods are, inter alia, all types of microscopy including staining of cell constituents. One example of direct staining is staining by specific antibodies which are directed against Plg-$R_{KT}$ and to which labeling signals such as, for example, fluorescent dyes are coupled. Detection methods are inter alia flow cytometry or FACS (fluorescence activated cell sorting), ELISA and Western blotting. Further methods for detecting Plg-$R_{KT}$ are inter alia nucleic acid detection methods with the aid of labeled probes, e.g. FISH, in situ hybridization, Northern, South-Western and Southern blotting or differential display, and inter alia nucleic acid amplification methods, inter alia PCR, RT-PCR, in situ RT-PCR, real-time PCT and NASBA.

The methods for detecting expression of Plg-$R_{KT}$ encompass the whole range of conventional diagnostic methods. Examples thereof are microscopic, immuno-cytological/immunocytochemical, biochemical and/or molecular biological methods.

It is possible for example to detect the expression of Plg-$R_{KT}$ after enrichment directly or after cell culture and expansion of the cells by morphological, immunocytological/immunocytochemical, biochemical and/or molecular biological methods as described above.

F. Therapeutic Compositions

The present invention contemplates therapeutic compositions useful for practicing the therapeutic methods described herein. Therapeutic compositions of the present invention contain a physiologically tolerable carrier together with an inhibitor of the binding of plasminogen, plasminogen fragments, tissue plasminogen activator or lipoprotein(a) to Plg-$R_{KT}$, namely a Plg-$R_{KT}$ polypeptide, an anti-Plg-$R_{KT}$ antibody or monoclonal antibody as described herein, dissolved or dispersed therein as an active ingredient. In a preferred embodiment, an inhibitor of the binding of plasminogen, plasminogen fragments, tissue plasminogen activator or lipoprotein(a) to Plg-$R_{KT}$ composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition contains a plasminogen, plasminogen fragments, tissue plasminogen activator or lipoprotein(a) binding to Plg-$R_{KT}$-inhibiting amount of an a plasminogen, plasminogen fragments, tissue plasminogen activator or lipoprotein(a) binding to Plg-$R_{KT}$ inhibitor of the present invention, typically an amount of at least 0.1 weight percent of inhibitor per weight of total therapeutic composition. A weight percent is a ratio by weight of inhibitor to total composition. Thus, for example, 0.1 weight percent is 0.1 grams of inhibitor per 100 grams of total composition.

G. Therapeutic Methods

It has been discovered that the Plg-$R_{KT}$ polypeptides, antibodies, and monoclonal antibodies of the present invention (i.e., inhibitors of plasminogen, plasminogen fragments, tissue plasminogen activator or lipoprotein(a) binding to Plg-$R_{KT}$) have the capacity to inhibit the binding of plasminogen and plasminogen fragments to Plg-$R_{KT}$. In view of the role of plasminogen binding to cells in inflammation, cancer and metastasis, and angiogenesis, and the like conditions where their binding to Plg-$R_{KT}$ is relevant to the condition, inhibition of plasminogen and plasminogen fragment binding to cells is expected to decrease such diseases and conditions.

Thus, the present invention provides for a method for blocking the binding of plasminogen, plasminogen fragments, tissue plasminogen activator or lipoprotein(a) to Plg-$R_{KT}$ on cells, and thereby reducing inflammation, cancer and metastasis, and angiogenesis, and the like, in a patient comprising administering to the patient a therapeutically effective amount of a physiologically tolerable composition containing a Plg-$R_{KT}$ polypeptide, antibody, or monoclonal antibody of the present invention.

A therapeutically effective amount of a Plg-$R_{KT}$ polypeptide, antibody, or monoclonal antibody inhibitor is a predetermined amount calculated to achieve the desired effect, i.e., to inhibit the in vivo plasminogen binding activity present in a patient and thereby decrease the amount of Plg-$R_{KT}$-mediated inflammation, cancer and metastasis, and angiogenesis occurring in the patient.

A therapeutically effective amount of a Plg-$R_{KT}$ polypeptide of this invention is typically an amount of a Plg-$R_{KT}$ polypeptide such that when administered in a physiologically tolerable composition is sufficient to achieve a plasma concentration of from about 0.1 micromolar (μM) to about 100 μM, and preferably from about 0.5 μM to about 10 uM.

A preferred embodiment of the present invention provides for a method for blocking the binding of plasminogen, plasminogen fragments, tissue plasminogen activator or lipoprotein(a) to Plg-$R_{KT}$ on cells, in a patient comprising administering to the patient a therapeutically effective amount of a physiologically tolerable composition containing a Plg-$R_{KT}$ polypeptide sufficient to achieve a plasma concentration of from about 0.1 micromolar (μM) to about 100 μM, and preferably from about 0.5 μM to about 10 μM.

The therapeutic compositions containing an Plg-$R_{KT}$ polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

A related embodiment of the present invention contemplates a composition comprising a Plg-$R_{KT}$ polypeptide (selected from the group of polypeptides according to claims 1-20) that inhibits plasminogen, plasminogen fragments, tissue plasminogen activator or lipoprotein(a) binding to Plg-$R_{KT}$.

A related embodiment of the present invention contemplates a composition comprising a Plg-$R_{KT}$ polypeptide (selected from the group of polypeptides according to claims 1-20) that inhibits plasminogen, plasminogen fragments, tissue plasminogen activator or lipoprotein(a) binding to Plg-$R_{KT}$ wherein the inhibiting amount is at least 0.1 weight percent Plg-$R_{KT}$ polypeptide per weight of total composition.

A further embodiment of the present invention contemplates a composition comprising a Plg-$R_{KT}$ polypeptide (selected from the group of polypeptides according to claims 1-20) that inhibits plasminogen, plasminogen fragments, tissue plasminogen activator or lipoprotein(a) binding to Plg-$R_{KT}$ wherein the inhibiting amount is at least 0.1 weight percent Plg-$R_{KT}$ polypeptide per weight of total composition and wherein the said Plg-$R_{KT}$ polypeptide is dispersed in a pharmaceutically acceptable excipient. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutically effective amount of an antibody of this invention is typically an amount of antibody such that when administered in a physiologically tolerable composition is sufficient to achieve a plasma concentration of from about 0.1 microgram (µg) per milliliter (ml) to about 100 µg/ml, preferably from about 1 µg/ml to about 5 µg/ml, and usually about 5 µg/ml.

A preferred embodiment of the present invention provides for a method for blocking the binding of plasminogen, plasminogen fragments, tissue plasminogen activator or lipoprotein(a) to Plg-$R_{KT}$ on cells, in a patient comprising administering to the patient a therapeutically effective amount of a physiologically tolerable composition containing an antibody according to claims 21 and 22 that is sufficient to achieve a plasma concentration of from about 0.1 microgram (µg) per milliliter (ml) to about 100 µg/ml, preferably from about 1 µg/ml to about 5 µg/ml, and usually about 5 µg/ml.

A preferred embodiment of the present invention contemplates a composition comprising a plasminogen, plasminogen fragments, tissue plasminogen activator or lipoprotein(a) binding to Plg-$R_{KT}$-inhibiting amount of antibody according to claims 21 and 22.

A related embodiment of the present invention contemplates composition wherein said plasminogen, plasminogen fragments, tissue plasminogen activator or lipoprotein(a) binding to Plg-$R_{KT}$-inhibiting amount of antibody (according to claims 21 and 22) is at least 0.1 weight percent antibody per weight of total composition.

A related embodiment of the present invention contemplates A further embodiment of the present invention contemplates a composition comprising plasminogen, plasminogen fragments, tissue plasminogen activator or lipoprotein(a) binding to Plg-$R_{KT}$-inhibiting amount of antibody (according to claims 21 and 22) wherein the concentration of antibody is at least 0.1 weight percent antibody per weight of total composition wherein the said Plg-$R_{KT}$-inhibiting amount antibody is dispersed in a pharmaceutically acceptable excipient. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The level of inhibition of Plg-$R_{KT}$ present in a patient indicative of the efficacy of Plg-$R_{KT}$ polypeptide, antibody, or monoclonal antibody inhibition therapy can be readily determined by routine clinical analysis. Exemplary assays to monitor the level of inhibition of plasminogen, plasminogen fragments, tissue plasminogen activator or lipoprotein(a) binding to Plg-$R_{KT}$ are described in Example 7.

As an aid to the administration of effective amounts of a Plg-$R_{KT}$ polypeptide, antibody, or monoclonal antibody a diagnostic method of this invention for detecting a Plg-$R_{KT}$ polypeptide, antibody, or monoclonal antibody, respectively, in the subject's blood is useful to characterize the fate of the administered therapeutic composition.

EXAMPLES

The following description provides details of the manner in which particular embodiments of the present invention may be made and used. This description, while exemplary of the present invention, is not to be construed as specifically limiting the invention. Variations and equivalents, now known or later developed, which would be within the understanding and technical competence of one skilled in this art are to be considered as falling within the scope of this invention.

1. Isolation of Plg-$R_{KT}$

Progenitor and M-CSF-differentiated Hoxa9-ER4 cells[22] ($5\times10^8$) were separately biotinylated, using EZ-Link Biotin-LCPEO-Amine (Pierce). The cells were then subjected to dead cell removal on annexin V-coated magnetic microspheres (Miltenyi) that resulted in a 99% enrichment of viable cells (as determined in FACS analysis with PI and annexin V). Membrane fractions were prepared from the viable cells by dounce homogenization in the presence of Complete Protease Inhibitor Cocktail (Roche, Palo Alto, Calif.) in Invitrosol (Invitrogen), followed by centrifugation steps as used in our laboratory [23,24] and 3 mg were applied to a 1 ml plasminogen-Sepharose affinity column as described [25]. The column was washed in phosphate buffered saline containing 1× Invitrosol until no protein was detected at 280 nm followed by elution with 0.2 M epsilon aminocaproic acid (EACA). The eluant from the plasminogen-Sepharose column was incubated with 50 µl of immobilized avidin for 30 minutes at 4° C. Proteins bound to the immobilized avidin were resuspended in 5 µl of Invitrosol and heated at 60° C. for 5 minutes. Then, 45 µl 80% acetonitrile were added and the samples were digested by trypsin at 37° C. for 18 h. After 24 h, the solvent was evaporated in a speedvac, and peptides were dissolved in 50 µl of buffer A (95% $H_2O$, 5% acetonitrile, and 0.1% formic acid).

The protein digest was subjected to multidimensional protein identification technology (MudPIT) [reviewed in [26]]. Peptide mixtures were resolved by strong cation exchange liquid chromatography upstream of reversed phase liquid chromatography [27-30]. Eluting peptides were electrosprayed into an LTQ ion trap mass spectrometer equipped with a nano-LC electrospray ionization source (ThermoFinnigan, San Jose, Calif.). Full MS spectra were recorded over a 400-1600 m/z range, followed by three tandem mass (MS/MS) events sequentially generated in a data-dependent manner on the first, second, and third most intense ions selected from the full MS spectrum (at 35% collision energy). Mass spectrometer scan functions and HPLC solvent gradients were controlled by the Xcalibur data system (ThermoFinnigan).

Tandem mass spectra were extracted from raw files, and a binary classifier [31], previously trained on a manually validated data set, was used to remove low quality MS/MS spectra. Remaining spectra were searched against a *Mus Musculus* protein database containing 50,370 protein sequences downloaded as FASTA-formatted sequences from EBI-IPI (database version 3.23, released on Nov. 2, 2006), and 124 common contaminant proteins, for a total of 66,743 target database sequences [32]. To calculate confidence levels and false positive rates, we used a decoy database containing the reverse sequences of the 66,743 proteins appended to the target database, and the SEQUEST algorithm [33] to find the best matching sequences from the combined database.

SEQUEST searches were done on an Intel Xeon 80-processor cluster running under the Linux operating system. The peptide mass search tolerance was set to 3 Da. No differential modifications were considered. No enzymatic cleavage conditions were imposed on the database search, so the search space included all candidate peptides whose theoretical mass fell within the 3 Da mass tolerance window, despite their tryptic status.

The validity of peptide/spectrum matches was assessed in DTASelect2 [34] using SEQUEST-defined parameters, the cross-correlation score (XCorr) and normalized difference in cross-correlation scores (DeltaCN). The search results were grouped by charge state (+1, +2, and +3) and tryptic status (fully tryptic, half-tryptic, and non-tryptic), resulting in 9 distinct sub-groups. In each one of the sub-groups, the distribution of XCorr and DeltaCN values for direct and decoy database hits was obtained, and the two subsets were separated by quadratic discriminant analysis. Outlier points in the two distributions (for example, matches with very low Xcorr but very high DeltaCN) were discarded. Full separation of the direct and decoy subsets is not generally possible; therefore, the discriminant score was set such that a false positive rate of 5% was determined based on the number of accepted decoy database peptides. This procedure was independently performed on each data subset, resulting in a false positive rate independent of tryptic status or charge state.

Initially, we probed the membrane proteome of M-CSF-differentiated Hoxa9-ER4 cells for the presence of a regulated integral membrane plasminogen receptor(s), exposing a C-terminal basic residue on the cell surface. Intact M-CSF-differentiated Hoxa9-ER4 cells were biotinylated as described above. Initially, using fluorescence activated cell sorting (FACS) analysis we verified that 1) viable cells were effectively biotinylated using anti-biotin fluorescein isothiocyanate (FITC)-labeled monoclonal antibodies, 2) specific plasminogen binding by the cells was not decreased when cells were treated with the biotinylating reagent and, 3) that biotinylated cells exhibited the same reduction in plasminogen binding capacity in response to carboxypeptidae B (CpB) as non-biotinylated cells, as criteria that the biotinylated plasminogen receptors were behaving as native plasminogen receptors. The membranes were isolated, subjected to affinity chromatography on plasminogen-Sepharose, digested with trypsin and subjected to MudPIT analysis, as described above. Using this method, only one protein with a predicted transmembrane sequence and a C-terminal basic residue was identified: the hypothetical protein, C9orf46 homolog (IPI00136293), homologous to the protein predicted to be encoded by human chromosome 9, open reading frame 46. Table 2 lists the peptides corresponding to C9orf46 homolog that were obtained when the membrane fraction from M-CSF-treated Hoxa9-ER4 cells was subjected to MudPIT. Our isolation of peptides corresponding to C9orf46 homolog is, to our knowledge, the first demonstration of the existence of this protein. We have designated the protein, Plg-$R_{KT}$, to indicate a plasminogen receptor with a C-terminal lysine and having a transmembrane domain (see below). No peptides corresponding to C9orf46 homolog/Plg-$R_{KT}$ were detected when biotinylated membrane fractions from undifferentiated progenitor Hoxa9-ER4 cells were subjected to the same purification method, suggesting that membrane expression of Plg-$R_{KT}$ was markedly upregulated by M-CSF treatment.

The C9orf46 homolog/Plg-$R_{KT}$ DNA sequence encodes a protein of 147 amino acids with a calculated molecular weight of 17,261 Da. The murine sequence is shown in SEQ ID NO:1. Notably, a carboxyl-terminal lysine is encoded. Correspondingly, when intact M-CSF-treated Hoxa9-ER4 cells were incubated with CpB prior to subcellular fractionation and purification, no peptides corresponding to C9orf46 homolog were detected. These data are consistent with exposure of the C-terminal lysine of Plg-$R_{KT}$ on the cell surface and, hence, accessibility to CpB [23,24], so that carboxypeptidase B treatment of intact cells resulted in loss of the ability of Plg-$R_{KT}$ to bind to the plasminogen-Sepharose column.

(Plasminogen binding to carboxyl terminal lysines on the cell surface is an important concept for understanding the identification of Plg-$R_{KT}$. The binding of plasminogen to cell surface proteins occurs via binding sites exposing carboxyl terminal lysines to the extracellular environment. Cell surface proteins with carboxyl terminal lysines that are masked or in other inaccessible orientations on the cell surface, or membrane-associated proteins with carboxyl terminal lysines that are located in the inner face of the membrane, cannot serve as plasminogen receptors. Carboxypeptidase B treatment of intact cells removes carboxyl terminal lysines from plasminogen receptors, and plasminogen binding to the cell surface is reduced.)

2. Amino Acid Sequence of Plg-$R_{KT}$

We blasted the C9orf46 homolog/Plg-$R_{KT}$ sequence against all species using NCBI Blast and obtained unique human, rat, dog and cow orthologs, with high homology (e.g. human versus mouse=96% homology), high identity and no gaps in the sequence Tables 3 and 4). Of key importance, a carboxyl-terminal lysine is predicted for all of the mammalian orthologs obtained in the blast search (Table 4). In a query of the Ensembl Gene Report, DNA sequences of all other available mammalian orthologs (armadillo, lesser Madagascar hedgehog, rhesus monkey, gray short tailed opossom, domestic rabbit and chimpanzee) encoded carboxyl-terminal lysines, supporting functional importance of this residue.

3. Cell and Tissue Distribution of Plg-$R_{KT}$

The C9orf46 homolog/Plg-$R_{KT}$ transcript is broadly expressed in normal human and mouse tissues, [as determined using high-throughput gene expression profiling in which RNA samples from human and murine tissues were hybridized to high-density gene expression arrays [17,18]] including spleen, thymus, lymph node, lung, intestine, bone marrow, as well as endocrine tissue, adrenal, pituitary vascular tissue, kidney, liver, stomach, bladder, and neuronal tissue (hippocampus, hypothalamus, cerebellum, cerebral cortex, olfactory bulb and dorsal root ganglion). In western blotting, we detected Plg-$R_{KT}$ in rat hippocampal neurons, bovine and mouse adrenal tissue and in rat pheochromocytoma PC12 cells in addition to expression in differentiated Hoxa9-ER4 cells in the current study.

We searched for C9orf46 homolog/Plg-$R_{KT}$ mRNA microarray expression data in the European Bioinformatics Institute ArrayExpress Archive database. C9orf46 homolog mRNA is present in monocytes, leukocytes, NK cells, T cells, myeloid, dendritic, and plasmacytoid cells, breast cancer, acute lymphoblastic leukemia and Molt-4 acute lymphoblastic leukemia cells. These data are consistent with previous reports documenting expression of plasminogen binding sites on peripheral blood leukocytes[19], breast cancer cells[8,20] and other tissues [reviewed in [16]]. In addition, results obtained by searching the ArrayExpress Warehouse indicated that the C9orf46 homolog gene is also regulated in other tissues by lipopolysaccharide, aldosterone, canrenoate, $H_2O_2$, and dexaamethasone. The broad distribution and regulation in tissues that express plasminogen binding sites, suggest that C9orf46 homolog/Plg-$R_{KT}$ provides plasminogen receptor function that may serve to modulate plasmin proteolytic functions in these tissues, as well. In genome-scale quantitative image analysis, overexpression of more than 86 cDNAs, including C9orf46 homolog, conferred dramatic increases in cell proliferation, while knockdown of C9orf46 homolog mRNA resulted in apoptosis[21]. In microarray studies, C9orf46 homolog mRNA expression has a high power to predict cervical lymph node metastasis in oral squamous cell carcinoma[35].

4. Plasminogen Binding to a Carboxyl Terminal Peptide of Plg-$R_{KT}$

Our isolation method was consistent with exposure of the carboxyl-terminus of Plg-$R_{KT}$ (with its carboxyl-terminal lysine) on the cell surface and also with the ability of the carboxyl-terminal domain to bind to plasminogen. For verification, we tested whether a synthetic peptide, corresponding to the C-terminus of Plg-$R_{KT}$ could bind plasminogen. The peptide, CEQSKLFSDK (SEQ ID NO: 33) corresponding to the ten C-terminal amino acids of Plg-$R_{KT}$ with cysteine substituted for $R_{138}$) was coupled to bovine serum albumin (BSA) and then coated onto wells of microtiter plates at 10 µg/ml. The wells were blocked with 5% BSA. Plasminogen (0.2 µM) was incubated with the wells, followed by our anti-plasminogen MAb [36] and detection with HRP-conjugated goat anti-mouse IgG (Biosource, Camarillo, Calif.). Plasminogen bound to the peptide in a concentration dependent manner with 50% maximal binding achieved at a plasminogen concentration of ~10 nM. The binding was specific because it was blocked in the presence of epsilon-aminocaproic acid (EACA), consistent with the ability of EACA to inhibit plasminogen binding to differentiated Hoxa9-ER4 cells. In additional controls, nonspecific binding to either BSA, or to the reverse peptide, KDSFLKSQEC (SEQ ID NO: 32), was <10% of binding to CEQSKLFSDK (SEQ ID NO: 33). In controls for the detection method, O.D.$_{490}$ values obtained using an isotype control antibody or in the absence of added plasminogen were <5% of the values for plasminogen binding to the BSA-coupled peptide detected with anti-plasminogen MAb.

5. Antibody Detection of Upregulation of Plg-$R_{KT}$ in Membranes of M-CSF-Treated Cells We raised an antiserum in rabbits against the synthetic peptide, CEQSKLFSDK (SEQ ID NO: 33). Membrane and cytoplasmic fractions from either untreated Hoxa9-ER4 cells or M-CSF-treated Hoxa9-ER4 cells (30 µg/lane) were electrophoresed and western blotted with either anti-peptide antiserum or preimmune serum. A specific immunoreactive band migrating with an $Mr_{app}$ of ~17,000 was detected by the antiserum in membranes from M-CSF-treated Hoxa9-ER4 cells. The band was not detected in membrane fractions from undifferentiated Hoxa9-ER4 cells or in cytoplasmic fractions from either undifferentiated or M-CSF-differentiated cells. The band was not detected in western blotting with pre-immune serum. These data further support the M-CSF-responsiveness and membrane localization of Plg-$R_{KT}$.

6. Partitioning of Plg-$R_{KT}$ Partitions to the Detergent Phase

To experimentally test the prediction that Plg-$R_{KT}$ is an integral membrane protein, M-CSF-differentiated Hoxa9ER-4 cells were subjected to phase separation in Triton X-114 as described [37,38]. In this technique, integral membrane proteins form mixed micelles with the nonionic detergent, and are recovered in the Triton X-114 detergent phase, whereas hydrophilic proteins remain in the aqueous phase. M-CSF-treated Hoxa9-ER4 cell membranes were solubilized in 3% Triton X-114. After heating at 37° C. and separation of the phases by centrifugation, an aliquot of both phases was electrophoresed and western blotted with anti-CEQSKLFSDK (SEQ ID NO: 33). antiserum. An immunoreactive band migrating with a $Mr_{app}$ of ~17,000, consistent with the predicted molecular weight of C9orf46 homolog/Plg-$R_{KT}$ was detected in the detergent phase, but was not detected in the aqueous phase, consistent with Plg-$R_{KT}$ being an integral membrane protein. In controls for the method, when the cell lysates were spiked with BSA and subjected to phase partitioning, BSA was detected in the aqueous, but not the detergent phase.

7. A monoclonal Antibody that Directly Binds to a Plg-$R_{KT}$ Polypeptide, Inhibits Plasminogen Binding to a Plg-$R_{Kt}$ Polypeptide and Inhibits Cell Surface Plasminogen Activation We raised a monoclonal antibody in rats against the Plg-$R_{KT}$ polypeptide, CEQSKLFSDK (SEQ ID NO: 33). Hybridomas were selected by the ability to bind directly to the same peptide coated on wells of microtiter plates, but not with the reverse peptide, KDSFLKSQEC (SEQ ID NO: 32). Hybridomas were further screened and selected for the ability to inhibit plasminogen binding to the Plg-$R_{KT}$ polypeptide, CEQSKLFSDK (SEQ ID NO: 33) and for the ability to react with a protein migrating at ~17 kDA in western blotting of M-CSF-treated Hoxa9-ER4 membranes. We identified several highly reactive hybridoma supernatants, and one of these, was subsequently cloned and developed as anti-Plg-$R_{KT}$ Mab36A12. Microtiter wells were coated with the Plg-$R_{KT}$ carboxyl-terminal peptide CEQSKLFSDK (SEQ ID NO: 33) coupled to BSA at 10 µg/ml. The wells were blocked with 5% BSA. Increasing concentrations of Mab36A12 or isotype control were added to the wells and incubated for 20 min at 22° C. Bound antibody was detected with HRP-conjugated goat anti rat IgG. Mab36A12 bound to the Plg-$R_{KT}$ polypeptide, CEQSKLFSDK (SEQ ID NO: 33) in a dose-dependent fashion and binding of the isotype control was not detected.

In addition Mab36A12 inhibited plasminogen binding to the Plg-$R_{KT}$ polypeptide, CEQSKLFSDK (SEQ ID NO: 33). Mab36A12 or control rat $IgG_{2A}$ was incubated with the Plg-$R_{KT}$ polypeptide, CEQSKLFSDK (SEQ ID NO: 33), coupled to BSA and immobilized on microtiter wells. In these assays, 200 nM biotinylated plasminogen was then added and plasminogen binding was detected with streptavidin-HRP. [Plasminogen directly bound to the peptide in a concentration-dependent manner and in controls for specificity, biotinylated-Plg binding was competed by unlabeled Plg and no biotinylated-Plg binding to the reverse peptide was detected.] Mab36A12 fully inhibited plasminogen binding to the Plg-$R_{KT}$ polypeptide, CEQSKLFSDK (SEQ ID NO: 33), with an $IC_{50}$ of 20 nM.

In plasminogen activation assays progenitor Hoxa9-ER4 cells ($1.5 \times 10^5$ cells/ml) were incubated with plasminogen and tissue plasminogen activator and plasminogen activation was determined on the tripeptide substrate, S-2251. In the presence of 20 μg/ml of the monoclonal antibody, Mab36A12, plasminogen activation was decreased by 30%, relative to the isotype control.

8. Inhibitory Plg-$R_{KT}$ Polypeptides

We tested the ability of a peptide, CEQSRFFIDK (SEQ ID NO: 34), corresponding to the C terminus of human Plg-$R_{KT}$ (residues 139-147), to inhibit the binding of biotinylated-plasminogen to the C-terminal peptide CEQSKLFSDK (SEQ ID NO: 33), of mouse Plg-$R_{KT}$ when CEQSKLFSDK (SEQ ID NO: 33), was coupled to BSA and immobilized to microtiter plates as described above. Plasminogen binding to the immobilized C-terminal peptide of Plg-$R_{KT}$ was inhibited in a dose-dependent manner by the peptide, CEQSRFFIDK (SEQ ID NO: 34), ($IC_{50}$=1 μM), but was not affected by a mutant peptide with the C-terminal K replaced with A, CEQSRFFIDA (SEQ ID NO: 35). Thus, the interaction of plasminogen with the C-terminal peptide of Plg-$R_{KT}$ requires the presence of a C-terminal lysine residue. In addition, a peptide with $R_{142}$ replaced with K CEQSRFFIDK (SEQ ID NO: 34), was a more effective competitor of biotinylated-plasminogen binding than the wild type peptide.

9. Recognition of Plg-$R_{KT}$ by Plasminogen Fragments in Other Assays to Define the ligand recognition specificity of Plg-$R_{KT}$ for plasminogen. the Plg-$R_{KT}$ polypeptide, CEQSKLFSDK (SEQ ID NO: 33), was coupled to microtiter wells. Plasminogen was directly biotinylated and then incubated with the immobilized peptide and detected with streptavidin-HRP, as above. (Plasminogen bound to the peptide in a concentration-dependent manner. In controls for specificity, biotinylated-Plg binding was competed by unlabeled Plg and no biotinylated-Plg binding to the reverse peptide was detected.) Plasminogen domains containing disulfide bonded kringle (K) structures were obtained by elastase digestion as described [39]. (K1-3 is comprised of the plasminogen amino acid sequences, $Tyr^{79}$-$Val^{337}$ or $Tyr^{79}$-$Val^{353}$. K4 is contained within the plasminogen amino acid sequences, $Val^{354}$-$Ala^{439}$. K5-PD is contained within the plasminogen amino acid sequences, $Val^{442}$-$Asn^{790}$ and contains kringle 5 as well as the latent protease domain.)

Plg domains containing kringle (K) structures inhibited the interaction with the following order of effectiveness: Plg>K1-3>K5>K4. Thus, kringle-containing domains of plasminogen, such as angiostatin, interact with the carboxyl terminus of Plg-$R_{KT}$. Notably, K1-3 and K5 express angiostatin activity.

10. A Monoclonal Antibody that Distinguishes Breast Cancer Cells from Normal Tissue We raised a monoclonal antibody in mice against the rat Plg-$R_{KT}$ polypeptide, CEQSKFFSDK (SEQ ID NO: 36). Hybridomas were selected by the ability to bind directly to the same peptide coated on wells of microtiter plates, but not with the reverse peptide. Hybridomas were further screened and selected for the ability to inhibit plasminogen binding to the Plg-$R_{KT}$ polypeptide, CEQSKFFSDK (SEQ ID NO: 36) and for the ability to react with a protein migrating at ~17 kDA in western blotting of M-CSF-treated Hoxa9-ER4 membranes. We identified several highly reactive hybridoma supernatants, and one of these, was subsequently cloned and developed as anti-Plg-$R_{KT}$ Mab7H1. In addition, Mab7H1 inhibited plasminogen binding to the Plg-$R_{KT}$ polypeptides, CEQSKLFSDK (SEQ ID NO: 33) and recognized the corresponding human, rat and mouse (SEQ ID NOs: 33-34, 36) sequences, inhibited plasminogen binding to these peptides and recognized the Plg-$R_{KT}$ protein (SEQ ID NO: 1) in western blotting.

We found very high expression of Plg-$R_{KT}$ in infiltrating ductal carcinoma in situ compared to normal adjacent tissue. For this experiment, a core from a case of infiltrating ductal carcinoma (Female 47: T3N3aMO: IIIC) from the Imgenex tissue array IMG-MH-364 was stained with MAb 7H1 using paraffin immunocytochemistry as described [40]. Staining was very high in the infiltrating ductal carcinoma tissue and was minimal in the normal adjacent tissue from this core. Correspondingly, minimal antibody staining was detected in normal breast ducts and lobules from a 60-year-old female control subject. In specificity control in which MAb 7H1 was absorbed with the Plg-$R_{KT}$ peptide used for immunization, [CEQSKFFSDK (SEQ ID NO: 36]), staining was not detectable. Thus, Plg-$R_{KT}$ is markedly expressed in infiltrating ductal carcinoma compared to normal breast ducts and lobules and Mab 7H1 can detect these differences in expression.

TABLE 2

Peptides obtained corresponding to C9orf46 homolog/Plg-$R_{KT}$

| Xcorr | DeltCN | Conf % | ObsM + H+ | CalcM + H+ | Peptide Sequences* |
|---|---|---|---|---|---|
| 3.8378 | 0.2884 | 99.8% | 2195.8743 | 2196.4788 | K.SMNENMKNQQEFMVTHAR.L (3+) (SEQ ID NO: 37) |
| 2.6749 | 0.1167 | 95.2% | 1359.5521 | 1361.5181 | K.NQQEFMVTHAR.L (2+) (SEQ ID NO: 38) |
| 2.6771 | 0.2534 | 99.8% | 1160.4321 | 1160.3514 | R.HLTMQNEMR.E (2+) (SEQ ID NO: 39) |
| 4.7468 | 0.3052 | 100% | 1523.5322 | 1523.6954 | R.MKSEAEDILETEK.T (2+) (SEQ ID NO: 40) |
| 5.1774 | 0.3788 | 100% | 2335.5544 | 2333.6997 | R.MKSEAEDILETEKTKLELPK.G (3+) (SEQ ID NO: 41) |
| 3.775 | 0.3164 | 100% | 1264.0922 | 1264.3287 | K.SEAEDILETEK.T (2+) (SEQ ID NO: 42) |
| 2.995 | 0.0655 | 96.8% | 1137.2722 | 1137.3184 | K.GLITFESLEK.A (2+) (SEQ ID NO: 43) |
| 2.893 | 0.2591 | 99.7% | 1364.4922 | 1364.5848 | K.GLITFESLEKAR.R (2+) (SEQ ID NO: 44) |

SEQUEST-defined parameters (Xcorr, DeltCN, and Conf %) are shown for each peptide. (core: cross-correlation score; DeltCN: normalized difference in cross-correlation scores; Conf %: confidence level of the peptide; ObsM + H+: observed peptide mass; CalcM + H+: theoretical peptide mass). Observed peptide mass, theoretical peptide mass, and charges of the peptide identified (3+ or 2+) are also shown to demonstrate accurate peptide identification.
*The exact peptide sequence obtained experimentally is delimited by periods (.). Residues before or after the periods (.) are those predicted from the DNA sequence of C9orf46 homolog.

TABLE 3

|  | Human | Rat | Dog | Bovine |
|---|---|---|---|---|
| A: % Interspecific amino acid sequence identities | | | | |
| Mouse | 82% | 95% | 85% | 76% |
| Human | — | 85% | 89% | 83% |
| Rat | — | — | 88% | 80% |
| Dog | — | — | — | 85% |
| B: % Interspecific amino acid sequence homologies | | | | |
| Mouse | 94% | 96% | 93% | 87% |
| Human | — | 97% | 98% | 94% |
| Rat | — | — | 96% | 91% |
| Dog | — | — | — | 94% |

TABLE 4

Alignment of predicted amino acid sequences of mouse, human, rat, dog and cow orthologs of Plg-$R_{KT}$

```
                1         10        20        30        40        50        60        70
                |         |         |         |         |         |         |         |

Mouse   MGFIFSKSMN ENMKNQQEFM VTHARLQLER HLTMQNEMRE RQMAMQIAWS REFLKYFGTF FGIATISLAT GALKR Human   MGFIFSKSMN ESMKNQKEFM LMNARLQLER QLIMQSEMRE RQMAMRIAWS REFLKYFGTF FGLAAISLTA GAIKK Rat     MGFIFSKSMN ENMKNQQEFM VMHARLQLER QLIMQNEMRE RQMAMQIAWS REFLKYFGTF FGIATISLAA GAIKR Dog     MGFIFSKSMN ENMKNQQEFM LMNARLQMER QLMMQNEMRE RQMAMQIAWS REFLKYFGTF FGIAAISLTA GAIRK Cow     MGFIFSKSMN ENLKSQQEFM LMNSRLQLER QLIMQNEMRE RQMAMQIAWS REFLKYFGTF FGITAVSLTA GAIKG 80        90        100       110       120       130       140       147
               |         |         |         |         |         |         |         |

Mouse   KKPAF LVPIVPLSFI FTYQYDLGYG TLLQRMKSEA EDILETEKTK LELPKGLITF ESLEKARREQ SKLFSDK (SEQ ID NO: 1)

Human   KKPAF LVPIVPLSFI LTYQYDLGYG TLLERMKGEA EDILETEKSK LQLPRGMITF ESIEKARKEQ SRFFIDK (SEQ ID NO: 45)

Rat     KKPAF LIPIVPLSFI FTYQYDLGYG TLLQRMKSEA EDILETEKTK LELPKGLITF ESLEKARREQ SKFFSDK (SEQ ID NO: 46)

Dog     KKPAF LFPIIPLSFI FTYQYDLGYG TLLQRMKGEA ENILETEKSK LQLPRGMITF ESLEKARREQ SKFFIDK (SEQ ID NO: 47)

Cow     KKPVL IFPIVPLGFV LAYQYDMGYG TLIHRMKGEA ENILETEKSK LQLPKGMITF ESLEKARKEQ SKFFIDK (SEQ ID NO: 48)
```

REFERENCE LIST (1) Miles L A, Dahlberg C M, Plow E F. The cell-binding domains of plasminogen and their function in plasma. J Biol Chem. 1988; 263:11928-11934.

(2) Saksela O. Plasminogen activation and regulation of pericellular proteolysis. Biochim Biophys Acta. 1985; 823:35-65.

(3) Testa J E, Quigley J P. Protease receptors on cell surfaces: New mechanistic formulas applied to an old problem. J Natl Cancer Inst. 1988; 80:712-713.

(4) Ploplis V A, French E L, Carmeliet P, Collen D, Plow E F. Plasminogen deficiency differentially affects recruitment of inflammatory cell populations in mice. Blood. 1998; 91:2005-2009.

(5) Lund L R, Bjorn S F, Sternlicht M D et al. Lactational competence and involution of the mouse mammary gland require plasminogen. Development. 2000; 127:4481-4492.

(6) Romer J, Bugge T H, Pyke C et al. Plasminogen and wound healing. Nature Med. 1996; 2:725.

(7) Creemers E, Cleutjens J, Smits J et al. Disruption of the plasminogen gene in mice abolishes wound healing after myocardial infarction. Am J Pathol. 2000; 156:1865-1873.

(8) Ranson M, Andronicos N M, O'Mullane M J, Baker M S. Increased plasminogen binding is associated with metastatic breast cancer cells: differential expression of plasminogen binding proteins. Br J Cancer. 1998; 77:1586-1597.

(9) Lopez-Alemany R, Suelves M, Munoz-Canoves P. Plasmin generation dependent on alpha-enolase-type plasminogen receptor is required for myogenesis. Thromb Haemost. 2003; 90:724-733.

(10) Jacovina A T, Zhong F, Khazanova E et al. Neuritogenesis and the nerve growth factor-induced differentiation of PC-12 cells requires annexin II-mediated plasmin generation. J Biol Chem. 2001; 276:49350-49358.

(11) Mitchell J W, Baik N, Castellino F J, Miles L A. Plasminogen inhibits TNF {alpha}-induced apoptosis in monocytes. Blood. 2006; 107:4383-4390.

(12) Swaisgood C M, Schmitt D, Eaton D, Plow E F. In vivo regulation of plasminogen function by plasma carboxypeptidase B. J Clin Invest. 2002; 110:1275-1282.

(13) Felez J, Miles L A, Fabregas P et al. Characterization of cellular binding sites and interactive regions within reactants required for enhancement of plasminogen activation by tPA on the surface of leukocytic cells. Thromb Haemost. 1996; 76:577-584.

(14) Felez J, Chanquia C J, Fabregas P, Plow E F, Miles L A. Competition between plasminogen and tissue plasminogen activator for cellular binding sites. Blood. 1993; 82:2433-2441.

(15) Miles L A, Fless G M, Levin E G, Scanu A M, Plow E F. A potential basis for the thrombotic risks associated with lipoprotein(a). Nature. 1989; 339:301-303.

(16) Miles L A, Hawley S B, Baik N et al. Plasminogen receptors: the sine qua non of cell surface plasminogen activation. Front Biosci. 2005; 10:1754-1762.

(17) Su A I, Cooke M P, Ching K A et al. Large-scale analysis of the human and mouse transcriptomes. Proc Natl Acad Sci USA. 2002; 99:4465-4470.

(18) Su A I, Wiltshire T, Batalov S et al. A gene atlas of the mouse and human protein-encoding transcriptomes. Proc Natl Acad Sci USA. 2004; 101:6062-6067.

(19) Miles L A, Plow E F. Receptor mediated binding of the fibrinolytic components, plasminogen and urokinase, to peripheral blood cells. Thromb Haemost. 1987; 58:936-942.

(20) Correc P, Fondanèche M-C, Bracke M, Burtin P. The presence of plasmin receptors on three mammary carcinoma MCF-7 sublines. Int J Cancer. 1990; 46:745-750.

(21) Harada J N, Bower K E, Orth A P et al. Identification of novel mammalian growth regulatory factors by genome-scale quantitative image analysis. Genome Res. 2005; 15:1136-1144.

(22) Wang G G, Calvo K R, Pasillas M P et al. Quantitative production of macrophages or neutrophils ex vivo using conditional Hoxb8. Nat Methods. 2006; 3:287-293.

(23) Hawley S B, Green M A, Miles L A. Discriminating between cell surface and intracellular plasminogen-binding proteins: heterogeneity in profibrinolytic plasminogen-binding proteins on monocytoid cells. Thromb Haemost. 2000; 84:882-890.

(24) Hawley S B, Tamura T, Miles L A. Purification, cloning, and characterization of a profibrinolytic plasminogen-binding protein, TIP49a. J Biol Chem. 2001; 276:179-186.

(25) Miles L A, Dahlberg C M, Plescia J et al. Role of cell-surface lysines in plasminogen binding to cells: Identification of alpha-Enolase as a candidate plasminogen receptor. Biochemistry. 1991; 30:1682-1691.

(26) Eng J K, McCormick A L, Yates J R I. An approach to correlate tandem mass spectral data of peptides with amino acid sequences in a protein database. J Am Soc Mass Spectrom. 1994; 5:976-989.

(27) Link A J, Eng J, Schieltz D M et al. Direct analysis of protein complexes using mass spectrometry. Nat. Biotechnol. 1999; 17:676-682.

(28) Larmann J P, Jr., Lemmo A V, Moore A W, Jr., Jorgenson J W. Two-dimensional separations of peptides and proteins by comprehensive liquid chromatography-capillary electrophoresis. Electrophoresis. 1993; 14:439-447.

(29) Opiteck G J, Jorgenson J W. Two-dimensional SEC/RPLC coupled to mass spectrometry for the analysis of peptides. Anal Chem. 1997; 69:2283-2291.

(30) Wolters D A, Washburn M P, Yates J R, III. An automated multidimensional protein identification technology for shotgun proteomics. Anal Chem. 2001; 73:5683-5690.

(31) Bern M, Goldberg D, McDonald W H, Yates J R3. Automatic quality assessment of peptide tandem mass spectra. Bioinformatics. 2004; 20, Suppl 1:149-154.

(32) Peng J, Elias J E, Thoreen C C, Licklider L J, Gygi S P. Evaluation of multidimensional chromatography coupled with tandem mass spectrometry (LC/LC-MS/MS) for large-scale protein analysis: the yeast proteome. J Proteome Res. 2003; 2:43-50.

(33) Yates J R, III. Database searching using mass spectrometry data. Electrophoresis. 1998; 19:893-900.

(34) Tabb D L, McDonald W H, Yates J R, III. DTASelect and Contrast: tools for assembling and comparing protein identifications from shotgun proteomics. J Proteome Res. 2002; 1:21-26.

(35) Nguyen S T, Hasegawa S, Tsuda H et al. Identification of a predictive gene expression signature of cervical lymph node metastasis in oral squamous cell carcinoma. Cancer Sci. 2007; 98:740-746.

(36) Pozzi A, Moberg P E, Miles L A et al. Elevated matrix metalloprotease and angiostatin levels in integrin alpha 1 knockout mice cause reduced tumor vascularization. Proc Natl Acad Sci USA. 2000; 97:2202-2207.

(37) Bordier C. Phase separation of integral membrane proteins in Triton X-114 solution. J Biol Chem. 1981; 256:1604-1607.

(38) Estreicher A, Wohlwend A, Belin D, Scleuning W-D, Vassalli J D. Characterization of the cellular binding site for the urokinase-type plasminogen activator. J Biol Chem. 1989; 264:1180-1189.

(39) Sottrup-Jensen L, Claeys H, Zajdel M, Petersen T E, Magnusson S. The primary structure of human plasminogen: Isolation of two lysine-binding fragments and one "mini-"plasminogen (MW 38,000) by elastase-catalyzed-specific limited proteolysis. In: Davidson J F, Rowan R M, Samama M M, Desnoyers P C, eds. Progress in Chemical Fibrinolysis and Thrombolysis, Vol. 3. New York: Raven Press; 1978:191-209.

(40) Krajewski S, Krajewska M, Ellerby L M et al. Release of caspase-9 from mitochondria during neuronal apoptosis and cerebral ischemia. Proc Natl Acad Sci USA. 1999; 96:5752-5757.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. An isolated antibody that immunoreacts with a Plasminogen ReceptorKT (Plg-RKT) polypeptide, the amino acid sequence of which comprises the sequence: TFESLEKARREQSKLFSDK (SEQ ID NO: 21), TEKTKLELPKGLITFESLEKARR (SEQ ID NO: 23), KRKKP (SEQ ID NO: 24) or XEQSXLFSDK (SEQ ID NO:16), wherein X at position 1 is K and X at position 5 is R; wherein the isolated antibody does not immunoreact with a polypeptide comprising the amino acid sequence AFLVPIVPLSFIFTYQYDLG (SEQ ID NO 31).

2. A therapeutic composition comprising the antibody of claim 1 and a pharmaceutically acceptable excipient.

* * * * *

UNITED STATES PATENT AND TRADEMARK OFFICE
CERTIFICATE OF CORRECTION

PATENT NO. : 8,314,212 B2  Page 1 of 4
APPLICATION NO. : 12/866520
DATED : November 20, 2012
INVENTOR(S) : Miles et al.

It is certified that error appears in the above-identified patent and that said Letters Patent is hereby corrected as shown below:

On the Title page, in Item (54), and in the specification, in column 1, line 1, in "Title", delete "PLG-RKT" insert --Plg-R$_{KT}$--, therefor On the Title page, in column 1, under "Other Publications", line 4, delete "suppl" and insert --suppl.--, therefor On the Title page, in column 2, under "Other Publications", line 14, delete "N," and insert --N.,--, therefor On the Title page, in column 2, under "Other Publications", line 17, delete "B," and insert --B.,--, therefor On the Title page, in column 2, under "Other Publications", line 21, delete "B," and insert --B.,--, therefor On the Title page, in column 2, under "Other Publications", line 24, delete "T," and insert --T.,--, therefor On the Title page, in column 2, under "Other Publications", line 29-30, delete "U S A." and insert --U.S.A.--, therefor On the Title page, in column 2, under "Other Publications", line 31, delete "J. P," and insert --J. P.,--, therefor On the Title page, in column 2, under "Other Publications", line 35, delete "J," and insert --J.,--, therefor On the Title page, in field (57), in "Abstract", in column 2, line 6, delete "plasminongen" and insert --plasminogen--, therefor Signed and Sealed this
Twenty-third Day of April, 2013

Teresa Stanek Rea
*Acting Director of the United States Patent and Trademark Office*

CERTIFICATE OF CORRECTION (continued)
U.S. Pat. No. 8,314,212 B2

On the Title page, in field (57), in "Abstract", in column 2, line 16, delete "plasminongen" and insert --plasminogen--, therefor On Title page 2, in column 1, under "Other Publications", line 4, delete "R," and insert --R.,--, therefor On Title page 2, in column 1, under "Other Publications", line 7, delete "A," and insert --A.,--, therefor On Title page 2, in column 1, under "Other Publications", line 9, delete "A," and insert --A.,--, therefor On Title page 2, in column 1, under "Other Publications", line 12, delete "A," and insert --A.,--, therefor On Title page 2, in column 1, under "Other Publications", line 15, delete "A," and insert --A.,--, therefor On Title page 2, in column 1, under "Other Publications", line 19, delete "A," and insert --A.,--, therefor On Title page 2, in column 1, under "Other Publications", line 22, delete "W," and insert --W.,--, therefor On Title page 2, in column 1, under "Other Publications", line 24, delete "T," and insert --T.,--, therefor On Title page 2, in column 1, under "Other Publications", line 27, delete "J," and insert --J.,--, therefor On Title page 2, in column 1, under "Other Publications", line 32, delete "Analysis:?" and insert --Analysis?--, therefor On Title page 2, in column 1, under "Other Publications", line 34, delete "A," and insert --A.,--, therefor On Title page 2, in column 1, under "Other Publications", line 38, delete "alpha 1" and insert --$\alpha$1--, therefor On Title page 2, in column 1, under "Other Publications", line 39, delete "U S A." and insert --U.S.A.--, therefor On Title page 2, in column 2, under "Other Publications", line 8, delete "J F," and insert --J. F.,--, therefor On Title page 2, in column 2, under "Other Publications", line 8, delete "R M," and insert --R. M.,--, therefor On Title page 2, in column 2, under "Other Publications", line 8, delete "M M," and insert --M. M.,-- therefor On Title page 2, in column 2, under "Other Publications", line 9, delete "P C," and insert --P. C.,-- therefor On Title page 2, in column 2, under "Other Publications", line 11, delete "I," and insert --I.,--, therefor On Title page 2, in column 2, under "Other Publications", line 12, delete "U S A.," and insert --U.S.A.,--, therefor On Title page 2, in column 2, under "Other Publications", line 14, delete "I," and insert --I.,--, therefor On Title page 2, in column 2, under "Other Publications", line 15, delete "U S A." and insert --U.S.A.--, therefor On Title page 2, in column 2, under "Other Publications", line 17, delete "M," and insert --M.,--, therefor On Title page 2, in column 2, under "Other Publications", line 20, delete "L," and insert --L.,--, therefor On Title page 2, in column 2, under "Other Publications", line 23, delete "E," and insert --E.,--, therefor On Title page 2, in column 2, under "Other Publications", line 26, delete "G," and insert --G.,--, therefor On Title page 2, in column 2, under "Other Publications", line 29, delete "A," and insert --A.,--, therefor On Title page 2, in column 2, under "Other Publications", line 32, delete "R," and insert --R.,--, therefor On Title page 2, in column 2, under "Other Publications", line 38, delete "hllp:llwww" and insert --http://www--, therefor On Title page 2, in column 2, under "Other Publications", line 41, delete "Rev iews" and insert --Reviews--, therefor On Title page 2, in column 2, under "Other Publications", line 43, delete "Pig-RKT" and insert --Plg-R$_{KT}$--, therefor

CERTIFICATE OF CORRECTION (continued)
U.S. Pat. No. 8,314,212 B2

On Title page 2, in column 2, under "Other Publications", line 43, delete "Journa l" and insert --Journal--, therefor On Title page 2, in column 2, under "Other Publications", line 46, delete "J,vol." and insert --J., vol.--, therefor In the Claims In column 63, line 20 (approx.), in Claim 1, delete "Plg-RKT" and insert --Plg-$R_{KT}$--, therefor

UNITED STATES PATENT AND TRADEMARK OFFICE
CERTIFICATE OF CORRECTION

PATENT NO. : 8,314,212 B2  
APPLICATION NO. : 12/866520  
DATED : November 20, 2012  
INVENTOR(S) : Miles et al.

Page 1 of 1

It is certified that error appears in the above-identified patent and that said Letters Patent is hereby corrected as shown below:

In the specification

In column 1, line 16-19, Delete "This invention was made with government support under Grant Nos. HL38272, HL45934 and HL081046, awarded by the National Heart, Lung, and Blood Institute, National Institutes of Health." and insert --This invention was made with government support under Grant Nos. HL38272, HL45934 and HL081046, awarded by the National Heart, Lung, and Blood Institute, National Institutes of Health. The government has certain rights in the invention.--, therefor Signed and Sealed this  
Ninth Day of February, 2016

Michelle K. Lee  
*Director of the United States Patent and Trademark Office*

SEQUENCE LISTING

```
<160> NUMBER OF SEQ ID NOS: 48

<210> SEQ ID NO 1
<211> LENGTH: 147
<212> TYPE: PRT
<213> ORGANISM: Mus musculus

<400> SEQUENCE: 1

Met Gly Phe Ile Phe Ser Lys Ser Met Asn Glu Asn Met Lys Asn Gln
 1               5                  10                  15

Gln Glu Phe Met Val Thr His Ala Arg Leu Gln Leu Glu Arg His Leu
            20                  25                  30

Thr Met Gln Asn Glu Met Arg Glu Arg Gln Met Ala Met Gln Ile Ala
        35                  40                  45

Trp Ser Arg Glu Phe Leu Lys Tyr Phe Gly Thr Phe Phe Gly Ile Ala
    50                  55                  60

Thr Ile Ser Leu Ala Thr Gly Ala Leu Lys Arg Lys Lys Pro Ala Phe
65                  70                  75                  80

Leu Val Pro Ile Val Pro Leu Ser Phe Ile Phe Thr Tyr Gln Tyr Asp
                85                  90                  95

Leu Gly Tyr Gly Thr Leu Leu Gln Arg Met Lys Ser Glu Ala Glu Asp
            100                 105                 110

Ile Leu Glu Thr Glu Lys Thr Lys Leu Glu Leu Pro Lys Gly Leu Ile
        115                 120                 125

Thr Phe Glu Ser Leu Glu Lys Ala Arg Arg Glu Gln Ser Lys Leu Phe
    130                 135                 140

Ser Asp Lys
145

<210> SEQ ID NO 2
<211> LENGTH: 43
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 21, 34, 38
<223> OTHER INFORMATION: Xaa = Lys or Arg

<400> SEQUENCE: 2

Arg Met Lys Ser Glu Ala Glu Asp Ile Leu Glu Thr Glu Lys Thr Lys
 1               5                  10                  15

Leu Glu Leu Pro Xaa Gly Leu Ile Thr Phe Glu Ser Leu Glu Lys Ala
            20                  25                  30

Arg Xaa Glu Gln Ser Xaa Leu Phe Ser Asp Lys
        35                  40

<210> SEQ ID NO 3
<211> LENGTH: 43
```

```
<212> TYPE: PRT
<213> ORGANISM: Mus musculus

<400> SEQUENCE: 3

Arg Met Lys Ser Glu Ala Glu Asp Ile Leu Glu Thr Glu Lys Thr Lys
 1               5                  10                  15

Leu Glu Leu Pro Lys Gly Leu Ile Thr Phe Glu Ser Leu Glu Lys Ala
                20                  25                  30

Arg Arg Glu Gln Ser Lys Leu Phe Ser Asp Lys
            35                  40

<210> SEQ ID NO 4
<211> LENGTH: 41
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 19, 32, 36
<223> OTHER INFORMATION: Xaa = Lys or Arg

<400> SEQUENCE: 4

Lys Ser Glu Ala Glu Asp Ile Leu Glu Thr Glu Lys Thr Lys Leu Glu
 1               5                  10                  15

Leu Pro Xaa Gly Leu Ile Thr Phe Glu Ser Leu Glu Lys Ala Arg Xaa
                20                  25                  30

Glu Gln Ser Xaa Leu Phe Ser Asp Lys
            35                  40

<210> SEQ ID NO 5
<211> LENGTH: 41
<212> TYPE: PRT
<213> ORGANISM: Mus musculus

<400> SEQUENCE: 5

Lys Ser Glu Ala Glu Asp Ile Leu Glu Thr Glu Lys Thr Lys Leu Glu
 1               5                  10                  15

Leu Pro Lys Gly Leu Ile Thr Phe Glu Ser Leu Glu Lys Ala Arg Arg
                20                  25                  30

Glu Gln Ser Lys Leu Phe Ser Asp Lys
            35                  40

<210> SEQ ID NO 6
<211> LENGTH: 30
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 8, 21, 25
<223> OTHER INFORMATION: Xaa = Lys or Arg

<400> SEQUENCE: 6

Lys Thr Lys Leu Glu Leu Pro Xaa Gly Leu Ile Thr Phe Glu Ser Leu
 1               5                  10                  15

Glu Lys Ala Arg Xaa Glu Gln Ser Xaa Leu Phe Ser Asp Lys
                20                  25                  30

<210> SEQ ID NO 7
<211> LENGTH: 30
<212> TYPE: PRT
<213> ORGANISM: Mus musculus
```

-continued

```
<400> SEQUENCE: 7

Lys Thr Lys Leu Glu Leu Pro Lys Gly Leu Ile Thr Phe Glu Ser Leu
 1               5                  10                  15

Glu Lys Ala Arg Arg Glu Gln Ser Lys Leu Phe Ser Asp Lys
            20                  25                  30

<210> SEQ ID NO 8
<211> LENGTH: 28
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 6, 19, 23
<223> OTHER INFORMATION: Xaa = Lys or Arg

<400> SEQUENCE: 8

Lys Leu Glu Leu Pro Xaa Gly Leu Ile Thr Phe Glu Ser Leu Glu Lys
 1               5                  10                  15

Ala Arg Xaa Glu Gln Ser Xaa Leu Phe Ser Asp Lys
            20                  25

<210> SEQ ID NO 9
<211> LENGTH: 28
<212> TYPE: PRT
<213> ORGANISM: Mus musculus

<400> SEQUENCE: 9

Lys Leu Glu Leu Pro Lys Gly Leu Ile Thr Phe Glu Ser Leu Glu Lys
 1               5                  10                  15

Ala Arg Arg Glu Gln Ser Lys Leu Phe Ser Asp Lys
            20                  25

<210> SEQ ID NO 10
<211> LENGTH: 23
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 1, 14, 18
<223> OTHER INFORMATION: Xaa = Lys or Arg

<400> SEQUENCE: 10

Xaa Gly Leu Ile Thr Phe Glu Ser Leu Glu Lys Ala Arg Xaa Glu Gln
 1               5                  10                  15

Ser Xaa Leu Phe Ser Asp Lys
            20

<210> SEQ ID NO 11
<211> LENGTH: 23
<212> TYPE: PRT
<213> ORGANISM: Mus musculus

<400> SEQUENCE: 11

Lys Gly Leu Ile Thr Phe Glu Ser Leu Glu Lys Ala Arg Arg Glu Gln
 1               5                  10                  15

Ser Lys Leu Phe Ser Asp Lys
            20

<210> SEQ ID NO 12
<211> LENGTH: 13
<212> TYPE: PRT
```

```
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 4, 8
<223> OTHER INFORMATION: Xaa = Lys or Arg

<400> SEQUENCE: 12

Lys Ala Arg Xaa Glu Gln Ser Xaa Leu Phe Ser Asp Lys
1               5                   10

<210> SEQ ID NO 13
<211> LENGTH: 13
<212> TYPE: PRT
<213> ORGANISM: Mus musculus

<400> SEQUENCE: 13

Lys Ala Arg Arg Glu Gln Ser Lys Leu Phe Ser Asp Lys
1               5                   10

<210> SEQ ID NO 14
<211> LENGTH: 11
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 2, 6
<223> OTHER INFORMATION: Xaa = Lys or Arg

<400> SEQUENCE: 14

Arg Xaa Glu Gln Ser Xaa Leu Phe Ser Asp Lys
1               5                   10

<210> SEQ ID NO 15
<211> LENGTH: 11
<212> TYPE: PRT
<213> ORGANISM: Mus musculus

<400> SEQUENCE: 15

Arg Arg Glu Gln Ser Lys Leu Phe Ser Asp Lys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 1, 5
<223> OTHER INFORMATION: Xaa = Lys or Arg

<400> SEQUENCE: 16

Xaa Glu Gln Ser Xaa Leu Phe Ser Asp Lys
1               5                   10

<210> SEQ ID NO 17
<211> LENGTH: 10
<212> TYPE: PRT
<213> ORGANISM: Mus musculus

<400> SEQUENCE: 17

Arg Glu Gln Ser Lys Leu Phe Ser Asp Lys
1               5                   10
```

```
<210> SEQ ID NO 18
<211> LENGTH: 6
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 1
<223> OTHER INFORMATION: Xaa = Lys or Arg

<400> SEQUENCE: 18

Xaa Leu Phe Ser Asp Lys
 1               5

<210> SEQ ID NO 19
<211> LENGTH: 6
<212> TYPE: PRT
<213> ORGANISM: Mus musculus

<400> SEQUENCE: 19

Lys Leu Phe Ser Asp Lys
 1               5

<210> SEQ ID NO 20
<211> LENGTH: 5
<212> TYPE: PRT
<213> ORGANISM: Mus musculus

<400> SEQUENCE: 20

Leu Phe Ser Asp Lys
 1               5

<210> SEQ ID NO 21
<211> LENGTH: 19
<212> TYPE: PRT
<213> ORGANISM: Mus musculus

<400> SEQUENCE: 21

Thr Phe Glu Ser Leu Glu Lys Ala Arg Arg Glu Gln Ser Lys Leu Phe
 1               5                  10                  15

Ser Asp Lys

<210> SEQ ID NO 22
<211> LENGTH: 21
<212> TYPE: PRT
<213> ORGANISM: Mus musculus

<400> SEQUENCE: 22

Gly Thr Leu Leu Gln Arg Met Lys Ser Glu Ala Glu Asp Ile Leu Glu
 1               5                  10                  15

Thr Glu Lys Thr Lys
                20

<210> SEQ ID NO 23
<211> LENGTH: 23
<212> TYPE: PRT
<213> ORGANISM: Mus musculus

<400> SEQUENCE: 23

Thr Glu Lys Thr Lys Leu Glu Leu Pro Lys Gly Leu Ile Thr Phe Glu
 1               5                  10                  15

Ser Leu Glu Lys Ala Arg Arg
                20
```

<210> SEQ ID NO 24
<211> LENGTH: 5
<212> TYPE: PRT
<213> ORGANISM: Mus musculus

<400> SEQUENCE: 24

Lys Arg Lys Lys Pro
1               5

<210> SEQ ID NO 25
<211> LENGTH: 20
<212> TYPE: PRT
<213> ORGANISM: Mus musculus

<400> SEQUENCE: 25

Met Gly Phe Ile Phe Ser Lys Ser Met Asn Glu Asn Met Lys Asn Gln
1               5                   10                  15

Gln Glu Phe Met
            20

<210> SEQ ID NO 26
<211> LENGTH: 21
<212> TYPE: PRT
<213> ORGANISM: Mus musculus

<400> SEQUENCE: 26

Asn Glu Asn Met Lys Asn Gln Gln Glu Phe Met Val Thr His Ala Arg
1               5                   10                  15

Leu Gln Leu Glu Arg
            20

<210> SEQ ID NO 27
<211> LENGTH: 21
<212> TYPE: PRT
<213> ORGANISM: Mus musculus

<400> SEQUENCE: 27

Met Val Thr His Ala Arg Leu Gln Leu Glu Arg His Leu Thr Met Gln
1               5                   10                  15

Asn Glu Met Arg Glu
            20

<210> SEQ ID NO 28
<211> LENGTH: 23
<212> TYPE: PRT
<213> ORGANISM: Mus musculus

<400> SEQUENCE: 28

Arg His Leu Thr Met Gln Asn Glu Met Arg Glu Arg Gln Met Ala Met
1               5                   10                  15

Gln Ile Ala Trp Ser Arg Glu
            20

<210> SEQ ID NO 29
<211> LENGTH: 23
<212> TYPE: PRT
<213> ORGANISM: Mus musculus

<400> SEQUENCE: 29

Glu Arg Gln Met Ala Met Gln Ile Ala Trp Ser Arg Glu Phe Leu Lys
1               5                   10                  15

Tyr Phe Gly Thr Phe Phe Gly
            20

```
<210> SEQ ID NO 30
<211> LENGTH: 24
<212> TYPE: PRT
<213> ORGANISM: Mus musculus

<400> SEQUENCE: 30

Ser Arg Glu Phe Leu Lys Tyr Phe Gly Thr Phe Phe Gly Ile Ala Thr
1               5                   10                  15

Ile Ser Leu Ala Thr Gly Ala Leu
            20

<210> SEQ ID NO 31
<211> LENGTH: 20
<212> TYPE: PRT
<213> ORGANISM: Mus musculus

<400> SEQUENCE: 31

Ala Phe Leu Val Pro Ile Val Pro Leu Ser Phe Ile Phe Thr Tyr Gln
1               5                   10                  15

Tyr Asp Leu Gly
            20

<210> SEQ ID NO 32
<211> LENGTH: 10
<212> TYPE: PRT
<213> ORGANISM: Mus musculus

<400> SEQUENCE: 32

Lys Asp Ser Phe Leu Lys Ser Gln Glu Cys
1               5                   10

<210> SEQ ID NO 33
<211> LENGTH: 10
<212> TYPE: PRT
<213> ORGANISM: Artificial Sequence
<220> FEATURE:
<223> OTHER INFORMATION: a synthetic peptide

<400> SEQUENCE: 33

Cys Glu Gln Ser Lys Leu Phe Ser Asp Lys
1               5                   10

<210> SEQ ID NO 34
<211> LENGTH: 10
<212> TYPE: PRT
<213> ORGANISM: Artificial Sequence
<220> FEATURE:
<223> OTHER INFORMATION: a synthetic peptide

<400> SEQUENCE: 34

Cys Glu Gln Ser Arg Phe Phe Ile Asp Lys
1               5                   10

<210> SEQ ID NO 35
<211> LENGTH: 10
<212> TYPE: PRT
<213> ORGANISM: Artificial Sequence
<220> FEATURE:
<223> OTHER INFORMATION: a synthetic peptide

<400> SEQUENCE: 35

Cys Glu Gln Ser Arg Phe Phe Ile Asp Ala
1               5                   10
```

```
<210> SEQ ID NO 36
<211> LENGTH: 10
<212> TYPE: PRT
<213> ORGANISM: Artificial Sequence
<220> FEATURE:
<223> OTHER INFORMATION: a synthetic peptide

<400> SEQUENCE: 36

Cys Glu Gln Ser Lys Phe Phe Ser Asp Lys
1               5                   10

<210> SEQ ID NO 37
<211> LENGTH: 20
<212> TYPE: PRT
<213> ORGANISM: Mus musculus

<400> SEQUENCE: 37

Lys Ser Met Asn Glu Asn Met Lys Asn Gln Gln Glu Phe Met Val Thr
1               5                   10                  15

His Ala Arg Leu
            20

<210> SEQ ID NO 38
<211> LENGTH: 13
<212> TYPE: PRT
<213> ORGANISM: Mus musculus

<400> SEQUENCE: 38

Lys Asn Gln Gln Glu Phe Met Val Thr His Ala Arg Leu
1               5                   10

<210> SEQ ID NO 39
<211> LENGTH: 11
<212> TYPE: PRT
<213> ORGANISM: Mus musculus

<400> SEQUENCE: 39

Arg His Leu Thr Met Gln Asn Glu Met Arg Glu
1               5                   10

<210> SEQ ID NO 40
<211> LENGTH: 15
<212> TYPE: PRT
<213> ORGANISM: Mus musculus

<400> SEQUENCE: 40

Arg Met Lys Ser Glu Ala Glu Asp Ile Leu Glu Thr Glu Lys Thr
1               5                   10                  15

<210> SEQ ID NO 41
<211> LENGTH: 22
<212> TYPE: PRT
<213> ORGANISM: Mus musculus

<400> SEQUENCE: 41

Arg Met Lys Ser Glu Ala Glu Asp Ile Leu Glu Thr Glu Lys Thr Lys
1               5                   10                  15

Leu Glu Leu Pro Lys Gly
            20

<210> SEQ ID NO 42
<211> LENGTH: 13
<212> TYPE: PRT
<213> ORGANISM: Mus musculus

<400> SEQUENCE: 42
```

Lys Ser Glu Ala Glu Asp Ile Leu Glu Thr Glu Lys Thr
1               5                   10

<210> SEQ ID NO 43
<211> LENGTH: 12
<212> TYPE: PRT
<213> ORGANISM: Mus musculus

<400> SEQUENCE: 43

Lys Gly Leu Ile Thr Phe Glu Ser Leu Glu Lys Ala
1               5                   10

<210> SEQ ID NO 44
<211> LENGTH: 14
<212> TYPE: PRT
<213> ORGANISM: Mus musculus

<400> SEQUENCE: 44

Lys Gly Leu Ile Thr Phe Glu Ser Leu Glu Lys Ala Arg Arg
1               5                   10

<210> SEQ ID NO 45
<211> LENGTH: 147
<212> TYPE: PRT
<213> ORGANISM: Homo sapiens

<400> SEQUENCE: 45

Met Gly Phe Ile Phe Ser Lys Ser Met Asn Glu Ser Met Lys Asn Gln
1               5                   10                  15

Lys Glu Phe Met Leu Met Asn Ala Arg Leu Gln Leu Glu Arg Gln Leu
                20                  25                  30

Ile Met Gln Ser Glu Met Arg Glu Arg Gln Met Ala Met Arg Ile Ala
            35                  40                  45

Trp Ser Arg Glu Phe Leu Lys Tyr Phe Gly Thr Phe Phe Gly Leu Ala
        50                  55                  60

Ala Ile Ser Leu Thr Ala Gly Ala Ile Lys Lys Lys Pro Ala Phe
65                  70                  75                  80

Leu Val Pro Ile Val Pro Leu Ser Phe Ile Leu Thr Tyr Gln Tyr Asp
                85                  90                  95

Leu Gly Tyr Gly Thr Leu Leu Glu Arg Met Lys Gly Glu Ala Glu Asp
            100                 105                 110

Ile Leu Glu Thr Glu Lys Ser Lys Leu Gln Leu Pro Arg Gly Met Ile
        115                 120                 125

Thr Phe Glu Ser Ile Glu Lys Ala Arg Lys Glu Gln Ser Arg Phe Phe
    130                 135                 140

Ile Asp Lys
145

<210> SEQ ID NO 46
<211> LENGTH: 147
<212> TYPE: PRT
<213> ORGANISM: Rattus norvegicus

<400> SEQUENCE: 46

Met Gly Phe Ile Phe Ser Lys Ser Met Asn Glu Asn Met Lys Asn Gln
1               5                   10                  15

Gln Glu Phe Met Val Met His Ala Arg Leu Gln Leu Glu Arg Gln Leu
                20                  25                  30

Ile Met Gln Asn Glu Met Arg Glu Arg Gln Met Ala Met Gln Ile Ala
            35                  40                  45

```
Trp Ser Arg Glu Phe Leu Lys Tyr Phe Gly Thr Phe Phe Gly Ile Ala
     50                  55                  60

Thr Ile Ser Leu Ala Ala Gly Ala Ile Arg Lys Lys Pro Ala Phe
 65                  70                  75                  80

Leu Ile Pro Ile Val Pro Leu Ser Phe Ile Phe Thr Tyr Gln Tyr Asp
                     85                  90                  95

Leu Gly Tyr Gly Thr Leu Leu Gln Arg Met Lys Ser Glu Ala Glu Asp
                 100                 105                 110

Ile Leu Glu Thr Glu Lys Thr Lys Leu Glu Leu Pro Lys Gly Leu Ile
             115                 120                 125

Thr Phe Glu Ser Leu Glu Lys Ala Arg Arg Glu Gln Ser Lys Phe Phe
130                 135                 140

Ser Asp Lys
145
```

```
<210> SEQ ID NO 47
<211> LENGTH: 147
<212> TYPE: PRT
<213> ORGANISM: Canis familiaris

<400> SEQUENCE: 47

Met Gly Phe Ile Phe Ser Lys Ser Met Asn Glu Asn Met Lys Asn Gln
 1               5                  10                  15

Gln Glu Phe Met Leu Met Asn Ala Arg Leu Gln Met Glu Arg Gln Leu
                 20                  25                  30

Met Met Gln Asn Glu Met Arg Glu Arg Gln Met Ala Met Gln Ile Ala
             35                  40                  45

Trp Ser Arg Glu Phe Leu Lys Tyr Phe Gly Thr Phe Phe Gly Ile Ala
     50                  55                  60

Ala Ile Ser Leu Thr Ala Gly Ala Ile Arg Lys Lys Pro Ala Phe
 65                  70                  75                  80

Leu Phe Pro Ile Ile Pro Leu Ser Phe Ile Phe Thr Tyr Gln Tyr Asp
                     85                  90                  95

Leu Gly Tyr Gly Thr Leu Leu Gln Arg Met Lys Gly Glu Ala Glu Asn
                 100                 105                 110

Ile Leu Glu Thr Glu Lys Ser Lys Leu Gln Leu Pro Arg Gly Met Ile
             115                 120                 125

Thr Phe Glu Ser Leu Glu Lys Ala Arg Arg Glu Gln Ser Lys Phe Phe
130                 135                 140

Ile Asp Lys
145
```

```
<210> SEQ ID NO 48
<211> LENGTH: 147
<212> TYPE: PRT
<213> ORGANISM: Bos taurus

<400> SEQUENCE: 48

Met Gly Phe Ile Phe Ser Lys Ser Met Asn Glu Asn Leu Lys Ser Gln
 1               5                  10                  15

Gln Glu Phe Met Leu Met Asn Ser Arg Leu Gln Leu Glu Arg Gln Leu
                 20                  25                  30

Ile Met Gln Asn Glu Met Arg Glu Arg Gln Met Ala Met Gln Ile Ala
             35                  40                  45

Trp Ser Arg Glu Phe Leu Lys Tyr Phe Gly Thr Phe Phe Gly Ile Thr
     50                  55                  60
```

-continued

```
Ala Val Ser Leu Thr Ala Gly Ala Ile Lys Gly Lys Lys Pro Val Leu
 65              70                  75              80

Ile Phe Pro Ile Val Pro Leu Gly Phe Val Leu Ala Tyr Gln Tyr Asp
             85                  90              95

Met Gly Tyr Gly Thr Leu Ile His Arg Met Lys Gly Glu Ala Glu Asn
            100             105             110

Ile Leu Glu Thr Glu Lys Ser Lys Leu Gln Leu Pro Lys Gly Met Ile
        115             120             125

Thr Phe Glu Ser Leu Glu Lys Ala Arg Lys Glu Gln Ser Lys Phe Phe
    130             135             140

Ile Asp Lys
145
```